(12) United States Patent
Schussler

(10) Patent No.: US 9,261,518 B2
(45) Date of Patent: Feb. 16, 2016

(54) METHOD FOR PRODUCING IMPLANTABLE MEDICAL BIOPROSTHESES HAVING REDUCED CALCIFICATION PROPERTIES

(76) Inventor: Olivier Schussler, Suresnes (FR)

( * ) Notice: Subject to any disclaimer, the term of this patent is extended or adjusted under 35 U.S.C. 154(b) by 227 days.

(21) Appl. No.: 13/499,688

(22) PCT Filed: Oct. 13, 2010

(86) PCT No.: PCT/FR2010/000683
§ 371 (c)(1),
(2), (4) Date: Mar. 31, 2012

(87) PCT Pub. No.: WO2011/051574
PCT Pub. Date: May 5, 2011

(65) Prior Publication Data
US 2012/0183971 A1    Jul. 19, 2012

(30) Foreign Application Priority Data

Oct. 15, 2009  (FR) ...................................... 09 57229

(51) Int. Cl.
*G01N 33/531* (2006.01)
*G01N 33/80* (2006.01)

(52) U.S. Cl.
CPC .............. *G01N 33/80* (2013.01); *G01N 33/531* (2013.01)

(58) Field of Classification Search
CPC .................................................... G01N 33/531
USPC ........................................................ 436/543
See application file for complete search history.

(56) References Cited

U.S. PATENT DOCUMENTS

| 5,662,704 | A * | 9/1997 | Gross ............................. 623/2.1 |
| 6,331,658 | B1 * | 12/2001 | Cooper et al. ................... 800/14 |
| 7,795,493 | B2 * | 9/2010 | Phelps et al. ..................... 800/17 |

OTHER PUBLICATIONS

Jamieson et al. (2005) Journal of Thoracic and Cardiovascular Surgery 130, pp. 994-1000.*
Balch C M et al: "Blood group compatibility and aortic valve allotransplantation in man" Journal of Thoracic and Cardiovascular Surgery, vol. 70, No. 2, 1975, pp. 256-259.
Jashari R et al: "Is ABO group incompatibility really the reason of accelerated failure of cryopreserved allografts in very young patients? Echography assessment of the European Homograft Bank (EHB) cryopreserved allografts used for reconstruction of the right ventricular outflow tract", Cell and Tissue Banking, Kluwer Academic Publishers, DO LNKD DOI:10.1007/510561-004-1442-Z, vol. 5, No. 4, Dec. 1, 2004, pp. 253-259.
Christenson Jan T et al: "Blood group incompatibility and accelerated homograft fibrocalcifications.", The Journal of Thoracic and Cardiovascular Surgery Jan. 2004 LNKD—Pubmed:14752436, vol. 127, No. 1, Jan. 2004, pp. 242-250.
Yankah et al:"Accelerated degeneration of allografts in the first two years of life", The Annals of Thoracic Surgery, Elsevier, vol. 60, Aug. 1, 1995, pp. S71-S77.
Shaddy Robert E et al: "Immunology and failure of valved allografts in children.", The Annals of Thoracic Surgery Oct. 2002 LNKD-Pubmed:12400797, vol. 74, No. 4, Oct. 2002, pp. 1271-1275.
Knosalla C et al: "Surgical treatment of active infective aortic valve endocarditis with associated periannular abscess: 11 Year results", European Heart Journal, vol. 21, No. 6, Mar. 2000, pp. 490-497.
Feingold B et al:"Expression of A and B Blood Group Antigens on Cryopreserved Homografts", The Annals of Thoracic Surgery, Elsevier LNKD DOI:10.1016/J.ATHORACSUR.2008.09.073, vol. 87, No. 1, Jan. 1, 2009, pp. 211-214.
International Search Report, Feb. 15, 2011, from International Phase of the instant application.

* cited by examiner

*Primary Examiner* — Ardin Marschel
(74) *Attorney, Agent, or Firm* — Young & Thompson

(57) ABSTRACT

The application relates to a method for producing a medical bioprosthesis that can be transplanted in a patient and comprises substances from animal tissue, said method comprising a step during which a bioprosthesis is positively selected for implantation in the body of said patient when (i) the phenotype in the ABO/ABH system of said bioprosthesis is compatible with (ii) the phenotype in the ABO/ABH system of said patient.

8 Claims, No Drawings

METHOD FOR PRODUCING IMPLANTABLE MEDICAL BIOPROSTHESES HAVING REDUCED CALCIFICATION PROPERTIES

SCOPE OF THE INVENTION

This invention relates to the field of implantable medical bioprostheses.

PRIOR ART

The implantable bioprostheses are known since many years. They mainly consist of prostheses made from animal tissue, which are intended to be implanted in a patient's body in order to overcome the dysfunction of a tissue, usually of a vascular or arterial conduit or even a heart valve.

Among the cardiac bioprostheses, mitral valves, aortic valves, pulmonary valves, tricuspid valves or even parietal repairing implants are particularly known. Among the vascular bioprostheses, aortic conduits or even pulmonary conduits are particularly known. Various other bioprostheses, such as "artificial" ligaments of knee, ankle or shoulder, etc is also known.

The implantable bioprostheses are made from animal tissues, mainly of tissue from bovine, porcine, ovine, or even tissues from kangaroos, seals, camels or equines. Animal tissues that have been chemically fixed, which include heart valves themselves, vessels, skin, dura mater, pericardium, ligaments, tendons, digestive submucous etc are widely used.

The implantable bioprostheses are used successfully in humans since at least forty years. In particular, bioprostheses have many advantages, compared to mechanical prostheses. Particularly, with bioprostheses, the risk of thrombosis observed with mechanical prostheses are not encountered. Thus, the use of bioprostheses offers patients great comfort in life and does not require treatment though anticoagulant agents likely to cause bleeding, unlike mechanical prostheses. Moreover, with the implantation duration, the operating efficiency of bioprostheses may reduce gradually, but without abrupt rupture for mechanical prostheses, which considerably limits the clinical consequences of a dysfunction for the patient. Moreover, non-invasive surgical techniques for implantation of bioprostheses are available today, particularly for replacement of heart valves.

For the reasons described above, bioprostheses are currently the prostheses which are most frequently used to overcome a dysfunction, especially cardiac or vascular.

Bioprostheses are prescribed most commonly in young patients, pregnant women and elderly patients.

However, the main drawback of bioprostheses is their low longevity in the patient's body, which rarely exceeds 15 years. On average, an aortic valve bioprostheses has a lifespan of 12 to 14 years.

The major cause of impairment of bioprostheses is in their degeneration, due to progressive calcification, which increases the thickness of the bioprosthetic tissue and impairs their mechanical properties, which prevents proper functioning and can cause their rupture, especially by tear (Tyers et al. (1995) *Ann Thorac Surg* 60, S464-468; discussion S468-469; Bortolotti et al. (1991). *J Card Surg* 6, 638-643; Grunkemeier, et al. (1995) *J Heart Valve Dis* 4, 49-55; Schoen, et al. (1984) *Cardiol Clin* 2, 717-739).

Because of this limited life span, bioprostheses are implanted primarily in individuals over age of 50 years. They are unsuitable for implantation in children. Bioprosthesis is the implant preferred for patients older than 70 years (Ueyama, et al. (2002). *Artif Organs* 26, 1059-1062). On the other hand, for subjects younger than 70 years, including the longevity of life is greater than the life span of the bioprosthesis, the use of implantation of a bioprosthesis has higher risks (Schoen, et al. (1999) Founder's Award, 25th Annual Meeting of the Society for Biomaterials, perspectives. Providence, R.I., Apr. 28-May 2, 1999. *J Biomed Mater Res* 47, 439-465). This is particularly true in young patients and children, in whom damage of the bioprosthesis is particularly fast (Williams, et al. (1982. *J Thorac Cardiovasc Surg* 84, 446-450; Rocchini et al. (1981) *Circulation* 64, II162-171). In newborns, bioprosthesis is impaired in less than 2 years. Unfortunately, there is currently no implant ideally suited for children.

The different factors which are involved in calcification of bioprostheses are not all established. The implicated factors are: (i) the patient's age at the time of implantation (Bortolotti, et al. (1991). *J Card Surg* 6, 638-643; Jamieson, et al. (1988). *Ann Thorac Surg* 46, 155-162), (ii) the existence of metabolic problems (such as hypercalcemia, hyperthyroid condition, diabetes, Paget's disease, etc.), parenteral administration of calcium, chronic renal failure (Schoen, and al. (1988) *J Biomed Mater Res* 22, 11-36), (iii) dietary factors, (iv) presence of an infection, (v) dehydration of the tissue at the time of insertion, (vi) mechanical stress particularly with distortions in the implantation or small aortic annulus, (vii) location of the site of implantation (aorta or mitral) (Jamieson, et al. (1995) *Ann Thorac Surg* 60, S235-240) (unfavorable implantation site in mitral position with greater mechanical stresses and systolic pressure regime during ventricular contraction while closing of sigmoid is done at aortic level in diastole during the cardiac relaxation), (viii) infection, (ix) chronic inflammation (calcification being the classic evolution of all inflammatory method in the body (see Tuberculosis, silicosis etc . . . ), (x) pregnancy (Jamieson, et al. (1995) *Ann Thorac Surg* 60, S282-286; discussion S287), (xi) the phase of growth in children (Silver, et al. (1980) *Am J Cardiol* 45, 685-689), and (xii) initial non optimal anticoagulation.

In young and children, it is possible that phosphocalcic metabolism greater than older patient is the source of particularly accelerated calcification of bioprostheses. However, Simionescu et al. (Simionescu, et al. (2004) *Expert Opin Biol Ther* 4, 1971-1985) made an analysis of numerous scientific works related to calcification of bioprostheses in children depending on the growth and adolescence. It appears that the impairment of bioprostheses occurs in an identical manner, before or after the growth phase, which suggests that other mechanisms like the simple phosphocalcic metabolism are likely to be implicated.

Different techniques have been used in order to overcome the drawbacks linked to limited lifespan of bioprostheses.

The mechanical stress suffered by the fixed tissue of bioprosthesis are especially attempted to be reduced, and implantation techniques to be improved, in order to avoid causing distortion of bioprosthesis during its implantation.

Other techniques consisted to improve the mechanical and/or chemical qualities of bioprostheses, particularly by perfecting the various treatments of animal tissue fixation from starting. Different methods have been proposed to improve the conventional technique of fixation by glutaraldehyde. For example, a post-fixation technique with a solution containing a mixture of alcohol/Tween/Formaldehyde was proposed, this technique being known as the sterilization procedure (Carpentier, et al. (1984) *Circulation*). The treatment of glutaraldehyde-fixed tissue by a surfactant without denaturant was also proposed (Patent Application US 2004/0093674). More recently, techniques combining treatment by glutaraldehyde fixation, adjuvant treatment by a surfactant or denaturant and a physical treatment by heat was also developed, during the stages of fixation (Patent applications US 2006/0217805; US 2005/0071926; US 2004/0030405; US 2003/0226208).

To limit the calcification of bioprostheses, treatments with crosslinking agents, other than glutaraldehyde (Ogle, et al. (2003) *Ann Thorac Surg* 75, 1267-1273; Chen, (1994) *Circulation* 90, 323-329; Vyavahare et al. (1997) *Circulation* 95, 479-488; Clark, et al. (2005) *Ann Thorac Surg* 79, 897-904) were also described.

Techniques for obtaining bioprostheses with improved geometry so as to reduce the mechanical stress suffered by the patient's body was also implemented. Also, for heart valves bioprostheses, bioprostheses without "stent" was developed, with the aim to limit the gradients of mechanical stress at the commissures (Hopkins, (2006) Circulation 114, 261-264; Schoen, et al. (1999) Founder's Award, 25th Annual Meeting of the Society for Biomaterials, perspectives. Providence, R.I., Apr. 28-May 2, 1999. *J Biomed Mater Res* 47, 439-46).

The above discussion illustrates the fact that numerous techniques have been developed in order to increase the lifespan of bioprostheses in the patient's body, including techniques aiming to reduce or delay calcification of biosprosthetic tissue.

Nevertheless, there always remains a need in the state-of-the-art for the availability of bioprostheses having an increased functioning longevity in the patients' bodies, particularly bioprostheses having reduced calcification properties, specifically for bioprostheses intended to be implanted in the body of young patients.

ABSTRACT OF THE INVENTION

This invention relates to a method for obtaining an implantable medical bioprosthesis in a patient comprising substances from animal tissue, comprising a step during which a bioprosthesis is positively selected for its implantation in the body of said patient when (i) the phenotype in ABO/ABH system of said bioprosthesis is compatible with (ii) the phenotype in ABO/ABH system of said patient.

This invention also relates to a method for obtaining an implantable medical bioprosthesis comprising substances from animal tissue, including the following steps:
  a) determine the phenotype in the ABO/ABH system of a patient in the body of which a bioprosthesis must be implanted,
  b) determine the phenotype in the ABO/ABH system of one candidate bioprosthesis, or in several candidate bioprostheses, and
  c) positively select a bioprosthesis for its implantation in the body of said patient when (i) the phenotype in the ABO/ABH system of said bioprosthesis is compatible with (ii) the phenotype in the ABO/ABH system of said patient,
the order of execution of steps a) and b) being indifferent.

The invention is also related to a method for obtaining an implantable medical bioprosthesis comprising substances from animal tissue including the following steps:
  a) provide several bioprostheses whose phenotype in the ABO/ABH system is known, and,
  b) positively select, within several of said bioprostheses, at least one bioprosthesis for its implantation in the body of said patient when (i) the phenotype in the ABO/ABH system of said bioprosthesis is compatible with (ii) the phenotype in the ABO/ABH system of said patient.

Generally, a bioprosthesis obtained by a method such as defined above has reduced calcification properties in a patient's body in which it must be implanted.

In some embodiments of said bioprostheses, the substances from animal tissue contained in a bioprosthesis are chosen among substances from mammal, preferably a mammal chosen among a porcine, bovine, ovine, equine, camel, seal and kangaroo.

Said bioprostheses can be chosen particularly among the bioprostheses of type heart valve, stented valves, any heart tissue including the valve leaflets, pericardial patch, ventricular restraint systems, coronary grafts, vascular prostheses with or without stent, central venous shunts, hybrid vascular grafts or no valvular rings, soft tissue such as gastrointestinal tract, skin, bladder, vascular conduits, conduits or wound tissue, inferior vena cava filters, access for hemodialysis, drainage system for eye glaucoma, endotracheal-bronchial tubes or stents, penile implants, orthopedic implants, dental implants, maxillofacial reconstruction devices, tendon prostheses, ligament prostheses, nerve regeneration tubes, patches, reconstituted tissues, active agents delivery devices (as described in patent application PCT/FR2008000785), arterial bioprostheses, vascular bioprostheses, pulmonary bioprostheses, replacement or regeneration tissue.

Said bioprostheses can particularly consist of heart valves chosen among the mitral, aortic, pulmonary and tricuspid valves.

In preferred embodiments of a method for obtaining medical bioprostheses in accordance with the invention, the said method may be further characterized in that the selection of a bioprosthesis is done according to the following compatibility rules:
  for patients whose ABO/ABH phenotype is the phenotype A, a bioprosthesis is positively selected, when the ABO/ABH phenotype of said bioprosthesis is a phenotype chosen among A or H,
  for patients whose ABO/ABH phenotype is the phenotype O, a prosthesis is positively selected, when the ABO/ABH phenotype of said bioprosthesis is the phenotype H,
  for patients whose ABO/ABH phenotype is the phenotype B, a prosthesis is positively selected, when the ABO/ABH phenotype of said bioprosthesis is a phenotype chosen among B (human) or H,
  for patients whose ABO/ABH phenotype is the phenotype AB, a prosthesis is positively selected, when the ABO/ABH phenotype of said bioprosthesis is a phenotype chosen among A, B or H, and
  for all patients, a prosthesis is selected positively, when the ABO/ABH phenotype of said bioprosthesis is not detectable.

In some embodiments, the said method is further characterized in that,
  the phenotype in the Rhesus system, respectively (i) for one or more candidate bioprosthesis and (ii) for the patient, is known or determined, and
  a bioprosthesis is positively selected when more than one compatibility is established for the phenotype in the Rhesus system.

In other embodiments, the said method is characterized in that,
  the phenotype in the Lewis or secretor system, respectively (i) for one or more candidate bioprosthesis and (ii) for the patient, is known or determined, and
  a bioprosthesis is positively selected when more than one compatibility is established for the phenotype in the Lewis system.

In the phenotype of Lewis system, bioprostheses of phenotype $le^{x-}/le^{y-}$ can be attributed according to the same selection criteria as for phenotype A;

bioprostheses of phenotype $le^{x-}/le^{y-}$ can be attributed according to the same selection criteria as for phenotype H;

bioprostheses of phenotype $le^{x-}/le^{y-}$ can be attributed according to the same selection criteria as for phenotype I (A–/H–/I).

In some embodiments, we can proceed to negative selection by systematically removing the bioprostheses of some ABH phenotypes, such as phenotype I bioprostheses (A–/H–/I).

DETAILED DESCRIPTION OF THE INVENTION

This invention provides new methods for obtaining implantable bioprostheses which have reduced calcification properties when they are implanted in the patient's body, and thus which have increased longevity properties.

Surprisingly, it was shown according to the invention that we could reduce, or delay in time, the phenomenon of calcification of implantable bioprostheses if, prior to the implantation surgical procedure, we proceeded to the selection of a prosthesis compatible with the recipient patient.

Specifically, it was shown according to the invention that we could reduce the phenomenon of calcification of a bioprosthesis, if said bioprosthesis implanted in a patient's body was previously selected according to its phenotype in the ABO/ABH system, so that the phenotype in the ABO/ABH system of said bioprosthesis is compatible with the phenotype in the ABO/ABH system of said patient.

It was particularly shown in the examples that, after a given duration of implantation in vivo, first bioprosthesis of ABO/ABH phenotype compatible with ABO/ABH phenotype of the mammal in which it was implanted had a calcium weight accumulation almost five times less than second bioprosthesis of phenotype identical to the first, but is not compatible with the ABO/ABH phenotype of the mammal in which this second bioprosthesis was implanted.

It was shown in the examples, from a multivariate statistical analysis conducted on a sample of 920 patients who received a bioprosthesis, that the compatibility of the ABO/ABH phenotype of the bioprosthesis with the ABO/ABH phenotype of the patient was the main predictive factor for longevity of an implanted bioprosthesis. In particular, the same multivariate statistical study shows that, surprisingly, the type of implanted bioprosthesis is not a relevant predictive factor for its longevity in the patient's body.

Also, it was shown in the examples that, in a sample of 920 patients in whom a bioprosthesis was implanted, and in patients with the highest probability of receiving a bioprosthesis of ABO/ABH phenotype compatible with their own ABO/ABH phenotype, the longevity of implanted bioprostheses was 2.33 years more than longevity of bioprostheses implanted in patients with other ABO/ABH phenotype.

It was also shown that, in a sample of 920 patients in whom a bioprosthesis was implanted, patients with a bioprosthesis preserved beyond 16 years were patients with the highest probability of receiving a bioprosthesis of ABO/ABH phenotype compatible with their own ABO/ABH phenotype.

It was also shown that that the ABO/ABH phenotype compatibility between the implanted bioprosthesis and the patient allowed to reduce, or delay in time, calcification of implanted bioprostheses. Thus, in a multivariate statistical study which is shown in the examples, calcified prostheses were found predominantly in patients with the highest probability of receiving a bioprosthesis of ABO/ABH phenotype incompatible with their own ABO/ABH phenotype.

It was shown in particular that, in a population of patients in whom a bioprosthesis has been implanted who had a longevity of more than sixteen years, all patients had received a bioprosthesis having a phenotype in the ABO/ABH system compatible with their own ABO/ABH phenotype. It was especially shown that all patients having received a bioprosthesis with great longevity of phenotype A, showed themselves the compatible phenotype A.

It results from the foregoing that increased longevity of bioprostheses in patients' bodies can be obtained when, prior to their implantation, bioprostheses are selected for their phenotypic compatibility in the ABO/ABH system with patients who are intended to receive them.

These results are even more surprising that, in the applicant's knowledge, any relationship between the physiological aspects of calcium metabolism and immune mechanisms has not been shown in the literature. It was clarified that the dysfunction of bioprostheses that occur over time are not similar to any mechanism of graft rejection of vascularized organs, as particularly witnessed by the implantation duration before dysfunctions, even precocious, which took place several years after implantation of bioprostheses, and for patients who are given no medical treatment for immunosuppressive activity.

This invention also relates to a method for obtaining an implantable medical bioprosthesis comprising substances from animal tissue, including a step during which a bioprosthesis is positively selected for its implantation in the body of said patient when (i) the phenotype in the ABO/ABH system of said bioprosthesis is compatible with (ii) the phenotype in the ABO/ABH system of said patient.

The above method can also be called "first method" in this description.

This invention also relates to a method for obtaining an implantable medical bioprosthesis comprising substances from animal tissue, including the following steps:

a) determine the phenotype in the ABO/ABH system of a patient in the body of which a bioprosthesis must be implanted, b) determine the phenotype in the ABO/ABH system of one candidate bioprosthesis, or in several candidate bioprostheses, and c) positively select a bioprosthesis for its implantation in the body of said patient when (i) the phenotype in the ABO/ABH system of said bioprosthesis is compatible with (ii) the phenotype in the ABO/ABH system of said patient, the order of execution of steps a) and b) being indifferent.
the bioprosthesis thus obtained with reduced calcification properties in a patient's body in which it must be implanted.

The above method can also be called "second method" in this description.

This invention is also related to a method for obtaining an implantable medical bioprosthesis comprising substances from animal tissue including the following steps:

a) provide several bioprostheses whose phenotype in the ABO/ABH system is known, and, b) positively select, within several of said bioprostheses, at least one bioprosthesis for its implantation in the body of said patient when (i) the phenotype in the ABO/ABH system of said bioprosthesis is compatible with (ii) the phenotype in the ABO/ABH system of said patient, the bioprosthesis thus obtained with reduced calcification properties in a patient's body in which it must be implanted The above method can also be called "third method" in this description.

Generally, a bioprosthesis obtained by any of the above methods has reduced calcification properties in a patient's body in which it is intended to be implanted.

The above methods can be collectively called "the method" or "methods" in this description. Those skilled in the art understand that the above first, second and third methods consist of alternatives of a general method for obtaining bioprosthesis.

By "implantable medical bioprosthesis", "implantable bioprosthesis" or "bioprosthesis", we mean a prosthesis according to the invention intended to be implanted in the human or animal body, and which is partially or entirely manufactured with animal tissue, said animal tissue having been treated chemically, biologically or physically, so as to give it desired appropriate physical, chemical or mechanical characteristics.

Bioprostheses include cardiac bioprostheses, which can be chosen especially among mitral valves, aortic valves, pulmonary valves, tricuspid valves or even parietal repair implants.

Bioprostheses also include vascular bioprostheses, which can be chosen especially among aortic conduits or even pulmonary conduits.

Bioprostheses also include artificial ligaments, including artificial ligaments of knee, ankle or shoulder, the valves fitted with or without a stent, cardiac tissue including the valve leaflets, pericardial patches, ventricular containment systems, coronary grafts, vascular prostheses with or without stent, central venous shunts, hybrid or non-hybrid vascular grafts, valvular rings, soft tissue such as gastrointestinal tract, skin, bladder, vascular conduits, conduits or wound tissue, inferior vena cava filters, access for hemodialysis, drainage system for eye glaucoma, endotracheal-bronchial tubes or stents, penile implants, orthopedic implants, dental implants, maxillofacial reconstruction devices, tendon prostheses, ligament prostheses, nerve regeneration tubes, patches, reconstituted tissues, active agents delivery devices (as described in patent application PCT/FR2008000785).

Various types of bioprostheses that can be used in the method for obtaining according to the invention, are described later in this description, particularly with reference to documents of the state-of-the-art which discloses them.

As known by those skilled in the art, the "substances" from animal tissue vary depending on the type of considered bioprosthesis. Said "substances" particularly include animal tissues themselves, including cardiac tissue, vascular tissue, skin, ligaments, tendons and tissue from digestive submucosa. Cardiac tissue covers heart valves and parietal cardiac tissue. Vascular tissue covers venous tissue and arterial tissue, including vessel conduits, venous conduits and arterial conduits.

In some implantable bioprostheses, "substances" from animal tissue include one or more components of the extracellular matrix, such as collagen.

The animals from which said substances some may also vary considerably depending on the type of considered bioprosthesis. Generally, the substances from mammal tissue are used. Most often, the substances from tissue of a mammal chosen among a porcine, bovine, ovine and equine are used. Most common bioprostheses, particularly cardiac bioprostheses, are made from tissue from porcine and bovines, preferably pig and ox.

Thus, in a method for obtaining an implantable medical bioprosthesis in accordance with the invention, the substances from animal tissue contained in a bioprosthesis are selected among substances from mammal, preferably a mammal selected among a porcine, bovine, ovine and equine.

By "Patient", we mean a human or non-human mammal according to the invention, which includes for example dogs, cats and horses.

By "ABO/ABH system", we mean the blood group system called "ABO" and "ABH" in humans and "ABH" in animals, especially porcines. The antigens of ABO/ABH system are expressed in most living tissues and not only on red blood cells, as this will be detailed later in this description. The antigens of ABO/ABH system can also be secreted and thus can be found circulating freely or well adsorbed on bodily substances or cell membranes. The phenotype of tissues in the ABO/ABH system usually belongs to one of four major groups respectively among groups A, B, AB and O. As detailed later, some individuals can have another phenotype, statistically minor in a population of individuals, the Bombay phenotype.

The techniques to determine the phenotype of a patient, in the ABO/ABH system are well known to those skilled in the art. For example, serological tests are widely used in which we determine the presence or absence of anti-A and anti-B antibodies in the patient. It is recalled that:
  in individuals with A phenotype, the presence of anti-B antibody and the absence of anti-A antibody is determined,
  in individuals with B phenotype, the presence of anti-A antibody and the absence of anti-B antibody is determined,
  in AB individuals, the absence of both anti-A and anti-B antibodies is determined,
  in O phenotype individuals, the presence of both anti-A and anti-B antibodies is determined.

Frequently, the tests for determining the phenotype of an individual in the ABO/ABH system are conducted according to immunodetection techniques well known to those skilled in the art, particularly:
  by determining the phenotype of red blood cells of the patient to be tested, using anti-A, anti-B antibodies and where appropriate also anti-H antibodies, or
  by determining the presence or absence of anti-A, or anti-B antibodies, using a support on which phenotype A or phenotype B antigens are immobilized, for example of red blood cells of known phenotype, or even supports suitable for immunological tests on which said antigens were immobilized according to known techniques.

To determine the phenotype of an implantable medical bioprosthesis in the ABO/ABH system, techniques of immunological tests known in themselves can be implemented, which include a step during which we brought into contact anti-A or anti-B or anti-H (anti-H1, anti-H2) or anti-I, anti-$Le^x$/anti-$Le^y$ antibodies, lectins (among other anti-H and/or anti-UE1 lectin *Ulex Europaeusl*, anti-I lectin like PNA *Arachis Hypogaea* (ref. Oriol R. Transplant International 1994)), with the surface of said bioprosthesis, or more generally with the material from animal tissue contained in said bioprosthesis.

To determine the phenotype of an implantable medical bioprosthesis in the ABO/ABH system, techniques for determining the genotype corresponding to the phenotype can also be implemented, in DNA amplification reactions using appropriate primers nucleic acid, possibly amplified DNA then being characterized by detection using suitable nucleotide probes. These genotypic detection techniques are well known to those skilled in the art and are now commonly performed in medical analysis laboratories, both in hospitals and analysis laboratories in private practice.

The rules of "compatibility" of phenotype ABO/ABH of the patient and phenotype ABO/ABH of a bioprosthesis respectively are those which are usually used in techniques for determining ABO/ABH compatibility in serology.

As shown in the examples, bioprostheses obtained in accordance with the above method have longevity in the body of patients which is on average significantly higher than the average longevity of prostheses that are often implanted these days. Without being bound by any theory, the applicant thinks that the difference in longevity observed in the examples between (i) bioprostheses compatible with the patient and (ii) bioprostheses not compatible with the patient is probably much lower than that which will be observed in practice, within the targeted clinical studies. This longevity property of the bioprosthesis in the patient's body already appears as a current predominant factor in the choice of allocation of bioprostheses, which goes far beyond all other known factors.

Through the method of the invention, it is now possible to perform bioprostheses implantations by restricting, in the population of treated patients, the impact of early alterations of, which occur after implantation duration less than seven years.

In the first method for obtaining an implantable medical bioprosthesis according to the invention, the essential characteristic remains in the technical step for positive selection of a bioprosthesis when (i) the phenotype in the ABO/ABH system of said bioprosthesis is compatible with (ii) the phenotype in the ABO/ABH system of said patient.

The implementation of said first method implicates that the phenotype in the ABO/ABH system of said patient has been previously determined.

In some embodiments of said first method, the phenotype in the ABO/ABH system of said bioprosthesis is also determined in advance, so as to allow the technical step for positive selection of a bioprosthesis that is compatible with the patient.

In other embodiments of said first method, "universal" bioprostheses are used, for which the phenotype in the ABO/ABH system is undetectable or even for the phenotype in the ABO/ABH system is type O, in which case, the technical step for positive selection essentially includes the fact to determine that all bioprostheses within which the selection must be made is referenced as being of "undetectable ABO/ABH" type or "O" type.

Symmetrically, those skilled in the art understand that the technical step for positive selection necessarily implies the realization of a technical step for negative selection with regard to a bioprosthesis whose phenotype in the ABO/ABH system is not compatible with the phenotype in the ABO/ABH system of the patient in whose body a medical bioprosthesis must be implanted.

It was specified that the technical characteristics described below for other methods for obtaining a medical bioprosthesis are directly transposable to the implementation of the above first method, since these characteristics relate to a step for positive selection of a bioprosthesis.

In the second method of obtaining an implantable medical bioprosthesis of the invention, which comprises three essential steps, the order of execution of steps a) and b) is indifferent. It is sufficient that, at the time of performing step c) for selection of a bioprosthesis compatible with the patient in whom it is intended, we know both the phenotype of said patient and the phenotype of said bioprosthesis, in the ABO/ABH system.

In some embodiments of the second method, step a) for determination of the phenotype of the patient may have been carried out until several years prior to step b) for determination of phenotype of said bioprosthesis, which does not present drawback, because the phenotype of a human or non-human mammal remains unchanged throughout its life.

In some embodiments of the second method, step b) can be performed prior to step a), for example in situations where a lot of bioprostheses, for which ABO/ABH phenotype was determined, was produced at a given time, until several months prior to implantation surgical procedure, and that the phenotype of recipient patient has been determined later, for example shortly before the decision for medical implantation of a bioprosthesis has been taken.

According to the third method for obtaining an implantable medical bioprosthesis defined above, several bioprostheses were provided whose phenotype in the ABO/ABH system was previously determined and is therefore known. According to this third method, the phenotype of recipient patient, in the ABO/ABH system, has also been determined in advance and is therefore also known. Thus, the essential step of third method of the invention consists, as for the first method above, to select, among the several bioprostheses, at least one bioprosthesis whose phenotype with ABO/ABH phenotype is compatible with the ABO/ABH phenotype of the recipient patient.

In some embodiments of a method for obtaining an implantable medical bioprosthesis in accordance with the invention, the fact that the ABO/ABH phenotype of said bioprosthesis is determined, can be materialized by the fact that the ABO/ABH phenotype of said bioprosthesis, or ABO/ABH phenotype of bioprostheses manufacturing lot to which it belongs, is recorded by the manufacturer. In some embodiments, the ABO/ABH phenotype of a bioprosthesis can be recorded on the packaging of such bioprosthesis, or even on the packaging of a lot containing several bioprostheses of the same ABO/ABH phenotype. In other embodiments, the ABO/ABH phenotype of the bioprosthesis can be recorded in a document accompanying the packaging of the bioprosthesis or even packaging of a lot comprising several bioprostheses. According to yet other embodiments, the ABO/ABH phenotype of the bioprosthesis is recorded in a document located at the manufacturer, or at the middleman supplying bioprostheses. According to these embodiments, the doctor may then, with the command of a bioprosthesis, declare the ABO/ABH phenotype of a patient to the supplier, who may be the manufacturer, so that the said supplier sends it a bioprosthesis compatible with the recipient patient, the compatible bioprosthesis being chosen by the said supplier from data of ABO/ABH phenotype of bioprostheses of which he is aware. In still other embodiments, the medical practitioner can have remote access to information of the ABO/ABH phenotype of a bioprosthesis, for example by online access to this information from the manufacturer or from any middleman approved by the manufacturer.

What is described above regarding the availability of information on ABO/ABH phenotype of a bioprosthesis is generalizable with the information of phenotype of said bioprosthesis, in other known compatibility systems, in the embodiments of the invention in which the phenotype in one or more of these other known compatibility systems constitutes a criterion for selection of said bioprosthesis.

If a phenotype of a colony, a group or breed of pigs is known, it will not be necessary to search the phenotype of each bioprosthesis, but allocation of the bioprosthesis according to only phenotype of the patient is enough.

In some embodiments of methods for obtaining bioprostheses according to the invention, said bioprostheses are chosen among heart valve type bioprostheses, arterial bioprostheses, vascular bioprostheses, a patch or tissue, pulmonary bioprostheses, replacement or regeneration tissues.

Replacement or regeneration tissues particularly include various tissues of the skin, like epidermis and dermis.

In some embodiments of methods for obtaining bioprostheses according to the invention, said bioprostheses consist of valvular bioprostheses chosen among the mitral, aortic, pulmonary and tricuspid valves.

In some embodiments of the methods of the invention, the ABO/ABH phenotype of a bioprosthesis is identical to the phenotype of the animal from which the tissue substances contained in the bioprosthesis come.

In some other embodiments of methods of the invention, the ABO/ABH phenotype of a bioprosthesis is distinct from the phenotype of the animal from which the tissue substances contained in the bioprosthesis come.

For example, in the bioprosthesis manufacturing method, some chemical, biological or physical treatments of animal tissue from starting are likely to impair the ABO/ABH antigens, which are sugars, such that ABO/ABH antigens initially expressed by the animal tissue become undetectable and the ABO/ABH phenotype of said bioprosthesis is therefore determined as being H phenotype.

In other examples, some chemical, biological or physical treatments of animal tissue from starting, during the bioprosthesis manufacturing method, have only partially impaired the ABO/ABH antigens, the ABO/ABH phenotype of said bioprosthesis being therefore finally determined as being H or I phenotype.

For the reasons above, it is essential that, in the methods of the invention, it is the ABO/ABH phenotype of the final bioprosthesis, in its form such as it will be implanted in the patient, who is determined, and not only the phenotype of the animal from which tissue substances come as said bioprosthesis includes.

In some embodiments of methods for obtaining an implantable medical bioprosthesis as defined in this present description, the selection of a bioprosthesis, in single step of the first method, in step c) of the second method or even in step b) of the third method, is carried out according to the following compatibility rules:
 for patients whose ABO/ABH phenotype is the phenotype A, a bioprosthesis is positively selected, when the ABO/ABH phenotype of said bioprosthesis is a phenotype chosen among A or H,
 for patients whose ABO/ABH phenotype is the phenotype O, a prosthesis is positively selected, when the ABO/ABH phenotype of said bioprosthesis is the phenotype H,
 for patients whose ABO/ABH phenotype is the phenotype B, a prosthesis is positively selected, when the ABO/ABH phenotype of said bioprosthesis is a phenotype chosen among B (human) or H,
 for patients whose ABO/ABH phenotype is the phenotype AB, a prosthesis is positively selected, when the ABO/ABH phenotype of said bioprosthesis is a phenotype chosen among A, B or H, and for all patients, a prosthesis is selected positively, when the ABO/ABH phenotype of said bioprosthesis is not detectable.

According to first aspect of the embodiments above, the methods of the invention are characterized in that the bioprostheses for which the ABO/ABH phenotype is not detectable are chosen among (i) bioprostheses comprising substances from an animal not expressing antigen of ABO/ABH system, including a genetically modified animal and (ii) bioprostheses having received one or more chemical, biological, physical or enzymatic treatments that caused impairment of antigens of the ABO/ABH system.

Animals not expressing antigen of the ABO/ABH system are preferably animals who have been genetically modified, especially animals whose genomic DNA has been artificially modified by genetic recombination techniques, in genes encoding enzymes catalyzing the synthesis of constituent sugars of the antigens of ABO/ABH system. Techniques for producing genetically modified animals of this type are for example described in the U.S. Pat. No. 7,126,039, but for an application for the supply of animal vascularized organs for implantation in humans without inducing hyperacute vascular rejection of xenogeneic graft.

Genetically modified animals include animals called "knock-out" for genes involved in the synthesis of ABO/ABH antigens. This can be transgenic animals for the human ABO/ABH system, particularly for the gene encoding the enzyme, the enzyme fucosyltransferase, or even glycosyltransferase, such as glycosyltransferase A1 and glycosyltransferase B. These genetically modified animals can also be knock-out for other sugar residues or other antigene involved in the rejection for alpha-galactosyltransferase enzyme, major enzyme for xenogeneic hyperacute rejection.

In some embodiments of the methods for obtaining an implantable medical bioprosthesis in accordance with the invention, the compatibility rules for the bioprosthesis in the recipient patient can still be refined by adding an additional requirement for compatibility in the Rhesus serological system well known to those skilled in the art.

Thus, in some embodiments of the methods of the invention, these methods are further characterized in that,
 the phenotype in the Rhesus system, respectively (i) for one or more candidate bioprosthesis and (ii) for the patient, is known or determined, and
 a bioprosthesis is positively selected when more than one compatibility is established for the phenotype in the Rhesus system.

For the phenotype in the Rhesus system, a bioprosthesis of Rh-positive phenotype will be positively selected, when the recipient patient is Rh-positive phenotype.

For the phenotype in the Rhesus system, a bioprosthesis of Rh-negative phenotype will be positively selected, when the recipient patient is Rh-positive or Rh-negative phenotype.

Through illustration, specific examples of compatibility rules between the bioprosthesis and the recipient patient are described below.

For O group patients, bioprostheses of phenotype A and also preferably I will be avoided. Bioprostheses of phenotype of A−/H+/I− will be preferably chosen while selecting as second option, if nothing else A−/H+/I+. It is therefore possible to offer group O patients phenotype H bioprostheses as described above.

For Group B patient, bioprostheses of phenotype A or I will be avoided. Bioprostheses of phenotype of A−/H+/I− will be thus chosen or A−/H+/I+ as second option. It is therefore possible to offer group B patients phenotype H or human B bioprostheses as described above.

AB group patients can receive bioprostheses of phenotype H, animal or human A or human B.

For Bombay group patients, bioprostheses of phenotypes H, B and AB will be avoided. These patients can benefit from bioprostheses on which we have reduced the expression of sugar residues overall.

Generally, the associated bioprostheses of phenotype I will be avoided.

There are two types of bioprostheses in group I: A−/H−/I+ bioprostheses and the bioprostheses or antigen I is either associated with antigen A or with antigen H. It is possible to distinguish these two groups due to the difference in sensitivity for detection of antigen I between anti I antibodies and lectin PNA. The anti-I antibodies recognizes the anti-I antibodies in A, H or I groups, while in most cases, lectin PNA does not recognize the antigen I when specificities A or H are expressed. It is therefore possible to eliminate the biocompatible phenotypes A−/H−I+ when the phenotype is recognized both by lectin and anti-I.

In yet other embodiments of the methods of the invention, these methods are characterized in that,
the phenotype in the Lewis system, respectively (i) for one or more candidate bioprosthesis and (ii) for the patient, is known or determined, and
a bioprosthesis is positively selected when more than one compatibility is established for the phenotype in the Lewis system.

Secretor and Lewis phenotypes of the patients are correlated with the presence of a FUT2 gene that is functional. This gene also encodes the type 2 H core. It can be also useful to offer pigs to the patients instead of H1 type 1 or rather H2 type according to Secretor or Lewis specific feature.

Often there exists a direct correlation between the phenotype A, H and I of bioprostheses and another antigen of ABH system like for example in the Lewis system. Animals of phenotype A+ (A+/H+/I− or A+/H−/I+) are generally $le^{x-}/le^{y-}$ phenotype. Animals of phenotype H(H+/A−/I+ or H+/A−/I−) are generally $le^{y+}/le^{x-}$ phenotype. Animals of phenotype I+(A−/H−/I+) are generally $le^{x+}/le^{y-}$. Thus when we allocate a bioprosthesis of phenotype:
A to a patient, this means allocating him a bioprosthesis of $le^{x-}/le^{y-}$ type.
H to a patient, this means allocating him a bioprosthesis of $le^{y+}/le^{x-}$ type.
I to a patient, this means allocating him a bioprosthesis of $le^{x+}/le^{y-}$ type.

Thus, in some cases it is possible, in the allocation, to replace a system of ABO/ABH group by a combination of another group of ABO/ABH system or all biological variable connected to this system.

Note that the animals that have H+ antigen generally do not have the I− antigen (in around 80% of cases).

In some additional embodiments of the methods for obtaining an implantable medical bioprosthesis, in accordance with the invention, a bioprosthesis is positively or negatively selected which is, in addition to its compatibility in the ABO/ABH system, also compatible with the phenotype of the patient in other compatibility systems, these other compatibility systems including the systems MNS, P, Lutheran, Kell, Duffy, Kidd, Diego, Cartwright, Xg, Scianna, Dombrock, Colton, Lansteiner-Wiener, Chido/Rodgers, Hh, Kx, Gerbich, Cromer, Knops, Indian, Okla., RAPH, John Milton Hagen, Ii, Globoside and GIL. (see Hosoi, E. (2008) Biological and clinical aspects of ABO blood group system. J Med Invest 55, 174-182)

In some additional embodiments of the methods for obtaining an implantable medical bioprosthesis, in accordance with the invention, a bioprosthesis is positively selected which is, in addition to its compatibility in the ABO/ABH system, also compatible with the phenotype of the patient in other compatibility systems, these other compatibility systems including the Rhesus systems (CED) (RHD genes, CE) (41), type of core H for groups A, B, AB or O for example (type H1, H2, H3, H4) (FUT genes), Secretor (SE, se) (secretor/non-secretor), Lewis (Lea, Leb, Lex) (FUT genes), Kell (KEL gene), Kidd (JK gene), Lutheran (LU gene), MNS, Duffy, Tn, T, Cad/sd, diego (DI) (AE1 gene), Cartwright (YT) (ACHE gene), Xg (XG) (XG gene), Scianna (SC) (SC gene), Dombrock (DO) (DO gene), Colton (CO) (AQP1 gene), LW (LW) (LW gene), Chido/Rodgers (CH/RG) (CH/RG gene), Kx (XK) (XK gene), Gerbich (GE) (GYPC gene), Cromer (CROM) (DAF gene), Knops (KN) (CR1 gene), Indian (IN) (CD44 gene), MN (glycophorin) Pk, etc. . . . for E. Hosoi review (2008)

Other characteristics of the invention are detailed below, that can be taken separately or in combination, according to considered embodiments.

Detailed Description of Compatibility Systems

The blood group antigens are sugar residues that are expressed at the surface of red blood cells. All red cell antigens are not necessarily synthesized by erythroblasts. For example Lewis antigens are adsorbed on erythrocytes from glycolipids transported in plasma. The best known antigens are ABO and Rhesus antigens but there are other blood group antigens such as Lewis, Kell, Duffy, Tn, T, Cad/sd, Pk, P etc. . . . antigens for E. Hosoi review (29) in 2008. Until recently, recognition of ABO group in humans was done by the ability of antibodies of their serum to agglutinate red blood cells having specific antigens. Thus, in human, according to its ABO blood group, there also exist natural antibodies in its serum directed against A antigens in group O or B persons, against B antigens in group A or O persons and finally the absence of these antibodies in group AB persons. In fact there are several groups A1, A2, B, O1, O2, AB. Between the groups A1 and A2 the sugar recognized is the same. This is more than one level of expression and localization of the antigen in tissues which is different (30). Because of the complexity of ABO groups, the molecular biology techniques (31-34) might replace the current technique by serology in few years. Indeed the ABO system in humans is a complex system which includes other specific features like among other Rhesus (85% are Rhesus+(DD or Dd), Lewis+ (Le(a+b−) or Le(a−b+)), Duffy, Kell, Kidd, Lutheran, MNS and secretor specific features. According to or not according to presence of the antigen, the individuals have or don't have antibodies vis-à-vis missing antigen in their blood. The count of these antibodies can increase after transfusion or pregnancy. The impact of different groups depends on ethnic origin. In the Caucasian population, the frequency of A and O groups is greater than 40-45% each, the frequency of B groups is less than 10%, and that of AB groups at around 3%. Group B in Asia represents 20% of the population and 15-20% in Africa. AB group represents 10-15% of the population in Asia.

ABO antigen is not only an antigen expressed on red blood cells. ABO group can be present in patients in the secretions like saliva secretion, or milk in the form of mucin. It is found on various circulating factors such as on coagulation proteins (Willebrand Factor). It is also expressed on numerous tissues, particularly glandular tissue, in endothelial and epithelial cells. Indeed, different factors influence the type, quantity and histological distribution of blood groups in the tissues, particularly ABO specificity, Lewis, secretor specificity or not, cells type and tissue type (35). In patients called "secretors" the ABO group is also expressed in the saliva or other secretions. They can also be expressed in keratinous appendages such as hair. With galactose of H antigen, a galactose is associated in the form of an alpha bonding 1,3 to form group B antigen (trisaccharide). If N-acetylgalactosamine is transferred on the H antigen galactose, group A trisaccharide antigen is formed. The formation of groups A and B is dependent on glycosyltransferase enzyme A or B encoded by the genes A and B. For group O individuals, these enzymes are not active. They express a specific enzyme in these individuals encoding for specificities O1 or O2 but this enzyme is not active due to deletion. There also exist two types of genes A1 and A2 which encode for galactosyltransferase A more or less active with more or less tissue expression of the antigen A. Different core H have been described, at least 4 in humans. The most common are types 1 and 2. The types 3 and 4 are found mostly in the gastrointestinal tract and in the respiratory epithelium. In humans as in pigs, group H of the epithelial cells of the stomach, H substances, are hydrocarbon structures carried by "O-glycosylated linked" proteins by GalNAc bridge to Ser or Thr on a surface protein (36).

Other antigens are linked to the ABO group such as Lewis and Rhesus, Kell, Duffy antigens. The Lewis specificity is formed under the action of a fucosyltransferase. Indeed, H, secretor and Lewis specificities are determined by addition of L-fucose on two main substrates whose characteristic pattern present at the end of glycan chains of various glycoconjugates is a disaccharide of type 1 (Galβ1-3GlcNAc) or type 2 (Galβ1-4GlcNAc) respectively. H fucosyltransferase catalyses the transfer of L-fucose (as GDPFuc) into position 1-2 on Galactose (Gal) of chains of type 2 mainly while fucosyltransferase participating in the patient's secretory phenotype SE transfers L-fucose into the same position on the chains of type 1 mainly. Fucosyltransferase participating in the development of Lewis specificity transfers L-Fucose on one hand into position α1-4 on N-acetylglucosamine (GlAc) of chains of type 1 and H of type 1 to form the products $Le^a$ and $Le^b$ respectively and on the other hand into position α1-3 on chains of type 2 and H of type 2 to form the products known under different nomenclatures: (CD15, X, $Le^x$) or (SSEA-1 and Y or $Le^y$).

The fucosyltransferases are in fact encoded by FUT genes (for review "JP Baron Towards a molecular approach of the structure, polymorphism and function of TCB blood groups (1996) 181-210"). Lewis specificity is actually encoded by a fucosyltransferase FUT 4-6 particularly FUT3. Other activities are encoded by fucosyltransferases as secretor or not type determined by another fucosyltransferase, fucosyl 2 encoded by FUT2 genes. The formation of group H type 1 involves mostly FUT2 and little FUT1. The formation of group H type 2 involves mostly FUT1 and little FUT2. H type 1: Galβ1-3GlcNAc-R with L-Fuc on α1-2 of Gal/H type 2: Galβ1-4GlcNAc-R with L-Fuc on α1-2 of Gal.

Lewis antigens can be "sialylated" particularly in chronic inflammatory or tumor tissues phenomena. The $Le^a$ antigen is encoded by FUT3. Secretor profile SE by FUT2. $Le^x$, CD15 (X, SSEA-1) by FUT4-6 but also FUT3 (LE). $Le^b$ by FUT3 and FUT2 or possibly FUT1. This explains why $Le^b$ are necessarly secretors, since the formation of antigen requires that FUT2 gene is active. Slex Sylil-type 2 involves FUT6; FUT7 or FUT5. In animals such as pig, animals of phenotype A+ are generally $le^{x-}/le^{y-}$. A−/H+ animals are generally $le^{y+}/le^{x-}$. A−/H−/I+ animals are generally $le^{x+}/le^{y-}$.

The above discussion illustrates how the type of H chain present in a human or an animal may be intimately linked to its secretor or non-secretor phenotype, in the Lewis system. In the animal, it has been shown that susceptibility to some infections or some behaviors were also correlated with the expression of some forms of fucosyltransferase.

Implantable Medical Bioprostheses Usable in Methods of the Invention

Implantable medical bioprostheses include any device intended to be implanted in humans and which contains animal tissue or animal synthesis products partially or completely, or components purified from animal tissue and cross-linked and/or fixed. The device can contain other autologous, homologous, synthetic or synthesized biological components. The device can be a tissue (for example U.S. Pat. Nos. 6,936,070, 5,067,962, 6,790,213, 4,585,458, 7,404,819, 20070254005), a matrix (for example U.S. Patent 20010051824, 20040157206, U.S. Pat. Nos. 6,652,583, 6,174,333, 5,855,620, 5,613,982), collagen (for example U.S. Patent 20030203008, U.S. Pat. Nos. 6,548,077, 6,127, 143, 5,814,328, 5,374,539), a conduit, a cardiac bioprostheses (for example 20090118826, U.S. Pat. Nos. 7,348,175, 20020173843, U.S. Pat. Nos. 5,824,061, 6,391,538, 7,316, 712, 20090030511, U.S. Pat. Nos. 6,719,789, 6,074,417, 7,011,681, 6,530,952, 5,824,067, 20040024452, U.S. Pat. Nos. 5,769,780, 4,692,164, 4,626,255, 20080154358, 2003010729, U.S. Pat. Nos. 7,331,993 7,503,930, 7,503,929, 6,997,950, 20030196274, 20030181974, 20030181974, U.S. Pat. Nos. 7,322,932, 6,027,530, 7,166,124, 7,163,556, 6,540, 781, 20010002445, U.S. Pat. No. 7,354,749, 20080095662, U.S. Pat. No. 5,545,214, 20040106991, U.S. Pat. No. 7,320, 705, 2004143323, U.S. Pat. Nos. 7,455,689, 5,662,704, 20030125805, 20030125793, U.S. Pat. Nos. 7,125,418, 7,125,418, 7,318,998, 7,041,132, 7,033,390, 6,719,785, 6,682,558, 6,087,552, 5,755,782, 5,571,174, 5,549,665, 5,545,215, 5,489,297, 5,352,240, 5,326,370, 5,728,152, 5,156,621, 5,080,670, 4,626,255, 4,561,129, 4,388,735, 4,378,224, 2008702554, 7,579,381, 7,214,344, 6,878,168, 6,561,970, 6,547,827, 6,214,054, 6,008,292, 5,935,168, 5,931,969, 5,931,969, 5,782,931, 5,215,541, 4,885,005, 4,838,888, 4,648,881, 4,647,283, 20060217805, 20040052830, 20030228692, U.S. Pat. Nos. 5,632,778, 5,613,982, 6,350,732, 20040136965, U.S. Pat. Nos. 7,129, 035, 7,014,655, 6,861,211, 7,438,850, 6,203,755, 20060207031, 20050071926, 20040253291, 20050010284, U.S. Pat. Nos. 6,322,593, 6,302,909, 6,231,614, 6,193,749, 6,177,514, 6,156,531, 6,156,531, 6,132,986, 6,093,530, 5,919,472, 5,094,661, 5,002,566, 4,976,733, 5,447,536, 5,368,608, 7,479,164, 5,733,339, 6,596,471, 30030196274, U.S. Pat. No. 7,156,881, 20020091445, U.S. Pat. Nos. 6,998, 418, 6,545,042, 7,014,655, 6,106,555, 5,080,670, 7,078,163, 6,509,145, 2003010746, U.S. Patent 5,935,168, 6,471,723, 6,350,732, 5,613,982), a heart valve, a patch (for example U.S. Pat. Nos. 20010051824, 20040157206, U.S. Pat. Nos. 6,652,583, 6,174,333, 5,855,620), a valvular prosthesis (for example U.S. Patent 20090118826; U.S. Pat. No. 5,545,215, WO/2000/047136), a scaffold as defined for example in PCT/ FR2008000785. It can be injectable. This can be a medium whose polymerization of some components produces spontaneously or after implantation or after photo-activation, ultraviolet irradiation, gamma irradiation, electric current, magnetic interaction, ionic interaction, chemical, enzymatic, biological, temperature, ultrasound, salt, hydrophobic/hydrophilic windings, van der Waals forces, aromatic binding π metal-ligand, pH, concentration, redox, phosphorylation, stacking, mechanical, electromagnetic or gravitational forces or association.

Within the invention, the implantable medical bioprostheses include all fixed heterologous tissue. Tissue/tissue extract/ collagen: the terms tissue or tissue extract or collagen can be used interchangeably and associated. It may be natural or synthetic. This tissue can be decellularized or not physically and/or enzymatically (for example with collagenase) and/or chemically modified or associated (like for example U.S. patent 20040052830, 20030228692, U.S. Pat. Nos. 5,632, 778, 5,613,982, 20010000804, 20050266390). This tissue can be compressed (for example U.S. Pat. No. 7,141,064). The tissue may be associated with synthetic component (like for example U.S. patent 20020172706, U.S. Pat. Nos. 6,596, 024, 6,562,069, 4,729,139, 4,481,009). The tissue may be cross-linked for example Sulfo/NHS (20060159641, U.S. Pat. No. 7,479,164) or by genipin (20020091445, U.S. Pat. No. 6,998,418) by the transglutaminase. The general methods of cross-linking have been described (US patent 20020177223). Cross-linking can be reversible voluntarily (US patent 20050244460).

The device can be a tissue like for example U.S. Pat. No. 7,189,259, a heart valve or a part of the heart, a vascular conduit like for example 20040158320, 20010020191, U.S. Pat. Nos. 6,358,275, 6,206,917, 6,110,212, 6,0875,52), a matrix like for example U.S. Patent 20040157206, U.S. Pat. Nos. 6,652,583, 6,174,333, 5,855,620), collagen (U.S. Patent 20030203008, U.S. Pat. Nos. 6,548,077, 6,127,143, 5,814,328, 5,374,539).

The tissue can be fixed so as to improve their properties, for example, physical, resistance to degradation, immunogenicity in general, its propensity to calcification, its thrombogenicity, its compliance, its resistance, its biological properties. It can be modified to alter its "ABH" antigenicity broadly to make it more compatible with "ABO" phenotype. For tissue extract the components of the extracellular matrix are included particularly such as proteins including collagen, elastin. Different method for purification of collagens has been proposed like for example (U.S. Patent 20030203008, U.S. Pat. Nos. 6,548,077, 6,127,143, 5,814,328, 5,374,539).

The collagen can be synthesized. The various components, including collagen, can be modified. The collagen term includes the various collagen types such as collagens (I, II, III, IV, V, VI, VII, XI and other collagens), or the association of different species. The term "collagen" also means insoluble collagen, soluble collagen, atelocollagen prepared by removing telopeptides on the ends of the collagen molecules using a protease other than collagenase. Collagen or tissues can be prepared from tissues such as ureter, pericardium, heart valves, digestive tissue like for example intestinal submucosa of pig "SIS" {Lindberg, 2001 #184; Badylak, 1998 #185}, blood vessel, tendon, fascia, decellularized or not decellularized dermis, aponeurosis, amniotic membrane-type membrane, dura mater, heart valve etc. . . . ). It could be synthetic copies of collagen such as polymer fibers or fibril-forming peptides. The collagen can be chemically modified and the product obtained by succinylation or esterification or formation of carboxyamides, or deamination of collagen described above, mixture of collagen with synthetic polymers such as poly-lactic acid) (PGA) and/or poly (DL-lactide-Co-glycolide) (PLGA) and/or poly (DL-lactide-Co-caprolactone) (PCL), a derivative of collagen such as gelatin, a polypeptide obtained by the hydrolysis of collagen, collagen denatured by heating. Synthetic polymers linked to collagen can be chosen among polylactic acid (PLA), polyglycolic acid (PGA), poly (L-lactic) (PLLA), PLGA, poly (anhydrides) (PA), polycarbonate (PC), hydroxy acids, poly ortho-esters (POE), propylfumarates) (PPF), polysaccharides, polylactone (PL), poly caprolactone, polyamides, polyamino acids, polyphosphazenes polyacetals (PPZ), biodegradable polycyanoacrylates, biodegradable polyurethanes (central unit), polysaccharides, polypyrrole, polyaniline, polythiophene, polystyrene, polyester (PE), non-biodegradable polyurethanes, polyureas, poly (ethylene terephthalate) (PET), poly (ethylene vinyl acetate), polypropylene, polymethacrylate, polyethylene, polycarbonates, poly ethylene oxide, polyvinyl alcohol (PVA), Gore-Tex (polytetrafluoroethylene), dacron (polyethylene terephthalate), polytetrafluoroethylene (PTFE), polyethylene glycol (PEG), copolymers described above, with one of the above additives, and mixtures of one of the polymers, copolymers, and additives between them and association of synthetic derivatives with biological products.

Collagen, tissue extract, can only be associated with synthetic, inorganic substances (such as glass, Si/SiO2, titanium/titanium oxide, gold, chromium, cobalt, diamond, platinum and hydroxyapatite, nitinol, steel, silica, streptavidine-biotin, an artificial protein such as latex, nylon, catguth, cotton, linen, polyester, silk, plastic, ceramic, alloys, textile, avidin, streptavidin, copolymer sponge-caprolactone-Co-L-lactide reinforced with poly-L-lactide, made of knitted tissue of hyaluronic acid (PCLA), starch and any mixture), biological organic materials (such as proteoglycans, glycoproteins, glycosaminoglycans, alginate, agarose, hyaluronic acid, agarose chitosan, fibrinogen/fibrin pair, carboxymethyl chitosan and mixture thereof, gelatin, sucrose octasulfate, dextran, cellulose, methylated cellulose, sepharose, protein imitated by Sephadex (such as latex) or their association.

Tissues can be chemically, enzymatically or physically modified. It can be associated with different molecules or bioactive agents including adhesion molecules, these different agents may or may not be attached to components of the tissue. Bioactive agents and adhesion molecules have been defined in international patent application (PCT/FR2008000785).

In the bioactive agents physical stimuli are included such as stress, heat, electromagnetic. It can be subjected to sterilization methods (for example U.S. Pat. Nos. 7,438,850, 6,203,755, 2008008906, U.S. Pat. Nos. 6,946,098, 6,908,591, 6,682,695, 6,036,918) and to treatments aiming to improve its conservation (for example U.S. patent 20040136965, U.S. Pat. Nos. 7,129,035, 7,014,655, 6,861,211). Different tissues and treatment can be associated.

Methods for Obtaining Animal Tissue of a Desired Phenotype, for the Manufacture of Implantable Medical Bioprostheses 1) Obtaining a Determined Porcine ABH/Human ABO-ABH Tissue:

"Human ABO-ABH system": By "ABO-ABH system" we mean different antigens of the ABO or ABH blood group system or human tissue in a broad sense as well as genes, the transcription products of these genes regulatory factors, sugars or sugar residues or antigens linked to these antigens and their regulators as well as all variable linked to the product for expression of these antigens, ABO group (32, 34, 37) or tissue ABH/Lewis/secretor (30, 38) of the recipient patient (35, 39, 40). ABO antigens are sugar residues carried by proteins or lipids. These are glycoproteins or glycolipids sugar residues in general. This is not only antigens of ABO blood system, but the family of these antigens expressed in the blood, but also in secretion products tissues, fluids. This may be ABO blood group system of the patient in a broad sense with different reported antigenic determinants which are not necessarily expressed on red blood cells but can be expressed in tissues or in secretion products, saliva, human fluid. These are ABO groups in a broad sense which contain more than 23 main systems according to international nomenclature of blood transfusion including (see A (A1, A2), B, AB, O) (ABO gene) but also other Rhesus specificities (CED) (RHD genes, CE) (41), type of core H for groups A, B, AB or O for example (type H1, H2, H3, H4) (FUT genes), Secretor (SE, se) (secretor/non-secretor), Lewis (Lea, Leb, Lex) (FUT genes), Kell (KEL gene), Kidd (JK gene), Lutheran (LU gene), MNS, Duffy, Tn, T, Cad/sd, diego (DI)(AE1 gene), Cartwright (YT) (ACHE gene), Xg (XG)(XG gene), Scianna (SC) (SC gene), Dombrock (DO) (DO Gene), Colton (CO) (AQP1 gene), LW (LW) (LW gene), Chido/Rodgers (CH/RG) (CH/RG gene), Kx (XK)(XK gene), Gerbich (GE)(GYPC gene), Cromer (CROM) (DAF gene), Knops (KN)(CR1 gene), Indian (IN) (CD44 gene), MN (glycophorin) Pk, etc. . . . for E. Hosoi review (2008)

There exist numerous mutations for these genes. One of these mutations corresponds to the absence of H chain in Bombay/Parabombay patients. It may be a mutation, a combination, a particulate expression for example in a particular tissue or a level of expression of these antigens. It can also be pseudogene associated with ABO system for example "htg4 human pseudogene". ABO group is represented by different antigens but also by the genes encoding for the different specificities or regulating their expression.

For example, the group A is mainly encoded by an enzyme A transferase, the group B by an enzyme B transferase. There exist at least two genes encoding for A transferase A1 and A2 that have different activity levels, where a tissue expression different from the antigen. The H specificity and Lewis and Secretor specificity are dependent on FUT type genes (42).

This can also be genes whose synthesis involves enzymes of the ABO system. These same genes are also involved in the production of specificities (CD15, X, $Le^x$) or (SSEA-1 or Y and $Le^y$). It can be antigens not appearing directly in ABO group but whose synthesis involves enzymes or genes or gene regulator of ABO group as sialyl Lea recognized by the antibodies CA19.9. (CD15, X, $Le^x$) or (SSEA-1 and Y or $Le^y$) or Forssman glycolipid synthetase antigen (33).

It can also be genes encoding for these different specificities or regulatory factors or modification of the expression of these different antigens or antigens correlated with the expression of some of these antigens. Same transcription factor, same location on the same gene or very close on the genome.

It can also be sugar antigen or not whose expression is correlated with some of these groups. More broadly, it can be patient's behavior or specific biological properties or not belonging to a subgroup of this ABO-ABH family.

ABH Phenotype of Animal Tissue:

By "ABH phenotype" of tissue we mean animal ABH system (43) which is the corollary of the ABO system in humans with an expression of antigens in the blood but mostly in tissues or secretion products or fluids. ABH the phenotype corresponds to that of the bioprosthesis at the time of its implantation. Change in the ABH phenotype if necessary can take place at any time during the manufacture of bioprosthesis. These sugar derivatives are generally expressed in the form of glycosphingolipid on the surface of epithelial cells in particular (44) N-linked (45) or in secretion mucins (see Julenius, {2005 #297}). Similarly, the method of attachment of group H on epithelial cells in pig (36) or in the secretions as mucin (46) (47) has been reported. If N-acetylgalactosamine is transferred on H antigen galactose, group A antigen trisaccharide is formed. The formation of groups A is dependent on an enzyme glycosyltransferase A encoded by transferase genes A identical to human A gene.

The invention offers a selection method for a patient of given blood group A, O, B, AB or Lewis blood or tissue ABH of a particular phenotype ABH/Lewis/secretor blood/tissue in the donor animal (43) particularly pig (48-51) or ox or horse knowing that the ABH antigens are expressed in most animal species. However, tissue expression of some antigens for example A, H, is variable depending on the species but also on the race for a species. It will be possible in this case to propose for a patient of ABO group in a broad sense given the preparation of implants from this or that race, the allocation is done with respect to the impact of the expression of desired antigen in the considered race. Nevertheless, the choice of allocation of the implant will consider the ABO group of the patient in a broad sense. It is also conceivable to have different colonies or clones of a determined animal having desired antigens or not expressing these antigens particularly in ABH blood group and tissue or not expressing some antigens of the ABH system. Here again, allocation of the choice of the implant will consider ABO blood system or tissue or variables linked to the patient.

Thus, ABH system exists in most mammals particularly in pig and in ox or horse or kangaroo or seal. In pigs, there are many A to L blood group antigen with different alleles of gene encoding for each of them. This ABH system can be searched non-exclusively in the blood, tissues particularly secretory tissues (urogenital system, digestive tract, salivary glands), products of saliva secretion, digestive proteins, milk etc. . . . by using immunological, histological or genetic or combination techniques. A useful approach is direct research of ABH group on salivary epithelial cells (51) since it is fast. Three types of genes are specifically expressed: antigen A, antigen H and antigen I. Antigen I is specific to pig. Antigen A and H are similar to human antigen A. Antigen B is different. Based on the studies of Oriol (43, 49) and of (51) and (52), there are overall 3 main phenotypes A+, H+ and I+ with impact 51%, 38% and 11% respectively. The classification is done based on the expression or not of antigenicity A. If absence of antigenicity A, presence or absence of antigenicity H. A and H negative pigs are generally of type I.

Phenotype A+ pigs are usually $le^{x-}/le^{y-}$. Phenotype H+ pigs are usually $le^{y+}/le^{x-}$. Phenotype I+ pigs are usually $le^{x+}/le^{y-}$. Generally there exists, especially in group A when the antigen H is expressed, absence of expression of antigen I.

Pigs of phenotype I+(A–/H–/I+) are both recognized by lectin PNA and anti-I antibodies. A+ and H+ pigs are pigs generally not recognized by lectin PNA. Recognition of antigen I in pigs of phenotype A+ and H+ is usually done using an anti-I antibody.

Obtaining Animal Tissue of "Human A Phenotype":

For animal A antigen, when it is expressed, there exists a complete similarity with the human A antigen. The specificity A is dependent on the A transferase enzyme. The easiest approach is the selection of animals expressing this specificity. We can possibly perform breeding with individuals having this specificity. For pigs with phenotype A, indeed there exist at least two types of pigs. A+ pigs and A+ and H+ pigs which thus express the sugar residue on a core H as in humans. Both types of pigs are useful even if the second type is more compatible.

The impact of A phenotypes depends on the porcine breed. For example, the impact of group A is 23% in Danish Landrace pigs, 35% in Hampshire breed and 49% in Duroc breed. Group H is 46% in Durocs, 29% in Danish Landrace and 13% in Hampshire. The expression of group I is in the range of 40-48% (see Andresen E. 1961 *PNAS Porcine Blood group antigens*).

For group A, the majority 52% expresses neither H nor I and are therefore A+/H–/I–. However, some number of pigs of this group A also express human H antigen and are thus very compatible for group A (A+/H+/I–) (16%), while others express I antigen and are thus less compatible A+/H–/I+ (31%).

Another approach is to obtain genetically modified pigs which express human A transferase specificity and use of tissues from these pigs to manufacture bioprostheses. This modification can further be accompanied by other genetic modifications of these pigs so as to particularly inhibit the expression of other sugar residues such as alpha-Gal antigens: alphaGal (Galα1,3Galβ1,4GlcNAcβ1-R) ("αGal") major antigen of vascular xenogeneic rejection (K Z. Konakci et al. (53)).

Obtaining Animal Tissue of "H Phenotype":

For H antigen, this is in some cases of human H antigen instead of type 1 or 2 depending on the tissue or the place where we search the antigen and pigs tested. We use anti-H, anti-H1 or H2 antibodies or other isotypes or lectins such as *Ulex Europaeus* 1, for example, or by genetics. The genes encoding H1 and H2 specificities are FUT1 and FUT2 genes which are fucosyltransferase. The H+ phenotype represent 38% of the pigs. For the H group, 78% are of true H (A−/H+/I−) but 22% also express the antigenicity I. On the other hand, H specificity is also present in 16% of pigs of group A (A+/H+/I−). H+ (A−/H+) pigs are generally $le^{y+}/le^{x-}$ and I+ or I− (I− generally). A+(A+/H+) pigs are also generally I−.

Thus, different approaches are also possible. The first consist to select the animals having a phenotype H. These are animals recognized particularly by anti-H antibodies, or animals recognized by the lectins that recognize the antigen H or $le^{x-}/le^{+}$ systems. The other solution is to perform negative selection by removing the animals that do not have phenotype H in their population, by removing phenotype I+ tissues ($le^{x+}/le^{y-}$ tissues or tissue) and tissues that react with anti-I lectin. So we find ourselves with a population enriched in phenotype A+/H−/I−, phenotype A+/H+/I− and phenotype A−/H+/I−. To obtain a population of phenotype A+/A− or H+/H+, it is possible to perform a negative selection of animals of phenotypes A−/H+ because these animals are usually of phenotype $le^{y+}/le^{x-}$. We can then remove individuals who do not react to antigen H or EUA1 and the remaining population will be then enriched in phenotype A+/H+/I− (this is an example of negative selection to obtain target phenotypes). Such a population is more "compatible" for a phenotype of valve intended to be implanted in humans. Another solution is to use tissues made from A+/H+ pig and to digest these tissues by an enzyme like for example alpha-D-Galactosidase so as to obtain tissue of type A−/H+. Techniques of digestion by exoglycosidase can also be used (54) (54).

Different approaches are also possible, like for group A it is possible to use transgenic animal tissues expressing some human genes encoding the core H particularly the FUT genes.

Obtaining Animal Tissue of "Human B Phenotype":

Contrary to H and B specificities, there exists no pig expressing human B specificities. However, in a group B patient, the tissues obtained from animals of H phenotype are well tolerated. It may be possible to generate transgenic animals expressing human B transferase activity.

Non-Selection of Some Animals Based on their ABH Phenotype:

Phenotyping of the pigs has dual use. Both to select the pigs having the useful antigen but also not to select pigs whose ABH antigenic specificity are less compatible with humans. Pigs of phenotype I (A−/H−/I+, A−/H+/−/I+ and A−/H+/I+) are particularly concerned. The antigen I+ can be easily identified by using the anti-I antibodies regardless of the group A+, H+ or I+, while the pigs I+ will be generally PNA+ or PNA and anti-I+ pigs.

Generally, we can either positively select the pigs for expression of antigen A+, H+ and I+ or $le^{y}/le^{y}$ specificities which are directly correlated with the expression of these phenotypes. Negative selection can be performed to increase the frequency of the antigen in the population to which we focus, for example in the choice of original breed, or by removing the animals of phenotype I+ (PNA+, anti I+), or by removing the animals expressing some antigens like antigen I (anti-I+ and PNA+/− animals). Another method of negative selection for the phenotype A, is to remove phenotypes H+ (recognized by antibodies H+ and lectin UEA+) and/or I+. It also comes to remove the phenotypes $le^{x+}/le^{y-}$ or $le^{x-}/le^{y+}$.

We can obtain H population H by negative selection while removing phenotypes A+ (anti-A) and I+ (anti-I and PNA+). H+ population can also be obtained by removing phenotypes $le^{y-}$.

For group I, the majority is A+/H−/I+, A−/H+/I+ or A−/H−/I+: 16%.

Obtaining Tissues Having Low Expression of ABH Antigen:

It is also possible in some cases to use enzymatic, chemical or physical means or associations aiming to remove the ABH antigens fixed on the tissues. However, in most cases this approach will impair the tissue properties.

The chemical structures of human type 1 and 2 cores H are well known and generally expressed in the form of glycosphingolipid on the surface of epithelial cells particularly (44) N-linked (45) or in Julenius secretion mucins, {2005 #297}. Similarly, the method of attachment of group H on epithelial cells in pigs (36) or in secretions in the form of mucin (46) (47) has been reported.

One of the approaches consists to use treatments aiming to free the H body from its support. Another approach consists to remove the lipidic or protidic patterns on which the patterns are attached. It is possible to make the core H disappear by using an enzyme such as neuraminidase (47 or alpha-L-fucosidase type enzyme. Another chemical method consists to make some sugar residues disappear from ABH system of the tissue as the method described by {Derevitskaya, 1983 #294) to fragment the core H of pig. Using chemical method to detach the core H by beta elimination of sugar chain followed by bromination of the enamine group resulting from cleavage of the amino acid residue brominated group by alkaline sodium borohydride technique used for fragmentation of core H of the pig (55). Possible use of a treatment by methanol-ethyl ether (1: 1, v/v) and chloroform-methanol (1: 1, v/v) (see K. Kishi and S. Iseki Immunochemical studies on blood group H and B substances from human hair). All these methods can be used on bioprostheses.

Use of genetically modified animals for porcine ABH system or expressing antigens of human ABO system:

In order to improve compatibility, we may use genetically modified pigs, particularly for ABH genes, to make them compatible with the human ABO system.

We can for example select pigs which do not express some blood group antigens conventionally expressed in pigs (for example A-L group antigens) or make pig genetically modified not to express such blood group antigen or sugar derivatives or variable linked to this antigen or to over-express some other antigen. This can also be a regulation in the expression of a blood group antigen with over or under expression. It is necessary to see that there is often a competition between different enzymes for production of blood group in their substrate. Thus, this and that sugar residue is generated in large quantity because another sugar antigen may be not expressed. Pig production do not express antigens such as antigen I for example.

Animals particularly pigs can be non-genetically modified animals. In this case, we will study the phenotypes of pigs and will select the pigs of interest by preferring if possible breeds or impact of the desired phenotype antigen is high or by selecting for a given species of interesting individuals or phenotype mutated for example or which would not express some ABH antigen of conventional pig phenotype.

We can also improve the compatibility of pigs by using transgenic pigs for human ABO system while making them particularly express the specific activity of a gene of the ABO system as for example human B transferase activity to make antigen B particularly in type H pigs. We can also make transgenic pigs to increase the expression of antigens H, A or B particularly in the desired tissues by modifying them genetically to express the gene human A transferase, B transferase or "fucozyltransferase" (FUT gene). We can also make KO pigs for some genes of porcine ABH system (see A to L antigens among others).

This change in ABH antigenicity can also be associated with a change in antigenicity vis-à-vis other antigenic patterns such as alphaGal sugar residues (Galα1,3Galβ1, 4GlcNAcβ1-R) ("αGal"). This can be obtained with genetically modified pigs such as KO pigs for the transmission of alpha Galactosyltransferase, or treat the tissue with enzymes such as alpha Galactosyltranferase, among others.

We can also use other modified pigs vis-à-vis sugar residues or antigens involved in the rejection such as of pigs not expressing the major antigen of vascular xenogeneic hyper acute rejection: alphaGal (Galα1,3Galβ1,4GlcNAcβ1-R) ("αGal").

These changes can be associated or paired with other methods aiming to modify the expression of other sugar residues or the expression of antigens on the surface of bioprostheses belonging or not belonging to the ABH system. This method can be paired with other approaches aiming to change the immunogenicity, calcification, physical properties, toxicity, biocompatibility, thrombogenicity of implanted tissues. Also the techniques aiming to improve the quality of fixation including its stability over time.

The various treatment approaches can be combined to have a porcine ABH/human ABO-ABH tissue of determined phenotype.

2) Attaching/Cross-linking the Tissue with Determined Animal ABH/Human ABO-ABH Phenotype:

The compatible animal ABH tissue is collected in a sterile manner and prepared for attachment and treatment. In the following invention, we propose to use the conventional attachment by glutaraldehyde but numerous changes in this attachment or the use of other attachment agents conventionally used to make bioprostheses can be used.

The tissue is washed with sterile water or PBS. The tissue can be treated with surfactant prior to fixation to remove lipids, fatty acids, cholesterol etc. (See U.S. Pat. No. 4,553, 974). Fixation of tissue in a solution of glutaraldehyde 0.625% pH 7.4 in phosphate buffer for 2 weeks fixation pressure less than 2 mmHg temperature control at 37° C. The tissue is then treated by a mixture of denaturant/surfactant/ crosslinking for 3 days (see 4% Formaldehyde, 2.2% Ethanol, 1.2% Tween 80 respectively).

Porcine tissue fixation by a treatment by glutaraldehyde and then treatment by Formaldehyde/Ethanol/Tween has been proposed since 1984 (6). Different fixations with glutaraldehyde have been proposed since, as well as various denaturants (for example US patent 20070255423). Anti-calcifying agents are often associated. Chemical pretreatments by aluminum chloride and/or ethanol are sometimes used. Surfactant can be used (see for example Dodecyl sulfate, alphaoleic acid, homocysteic acid/US Patent. 20060154230). The tissue can then be sterilized (for example U.S. Pat. Nos. 743,850, 6,203,755) and preservation solutions can be used (for example U.S. Pat. Nos. 5,935,168, 20040136965, U.S. Pat. Nos. 7,129,035, 7,014,655, 6,861,211, 7,579,381, 7,214, 344, 6,878,168, 6,561,970, 6,547,827, 6,214,054, 6,008,292, 5,935,168, 5,931,969, 5,782,931, 5,215,541, 4,885,005, 4,838,888, 4,648,881, 4,647,283). Of course other fixation methods or variants of this fixation can be used with pH variation of glutaraldehyde fixation, use of a reducing agent, heat fixation, etc. (For example U.S. Pat. Nos. 7,579,381, 7,214,344, 6,878,168, 6,561,970, 6,547,827, 6,214,054, 6,008,292, 5,935,168, 5,931,969, 5,782,931, 5,215,521, 4,885,005, 4,838,888, 4,648,881, 4,647,283, 20070255423, 20060217805, 20040253291, 20070255423, 20050071926, U.S. Pat. No. 7,214,344, 20090164005).

Other cross-linking agents: this polymerization or cross-linking can result from a chemical reaction with known cross-linking agents and derivatives and/or their analogues, derivatives and combination as for example genipin, aglycone of nordihydroguaiaretic acid, geniposidic acid, epoxy compounds, dialdehyde starch, glutaraldehyde, formaldehyde, dimethyl suberimidate, carbodiimide, acyl azide, "dye mediated photo-oxidation", succinimidyl, diisocyanate, acyl azide, glyceraldehyde, cyanamide, diimides, dimethyl adipimidate, ruterine, nordihydroguaiaretic acid, enzymatic transformation, thrombin, dehydrothermal treatment, endogenous cross-linking by cells and their normal biochemical products (such as lysine oxidase produced by a cell . . . ), methods aiming to remove unbound glutaraldehyde or to reduce the release of glutaraldehyde residues by blocking with an amine component as for example the use of diphosphonates fixed on tissue previously fixed with glutaraldehyde or given directly in the treated tissue, acid substituted with aliphatic group "amino-substituted aliphatic functional acid" covalently fixed to tissue fixed in glutaraldehyde, iron-rich or stannic salts before or after glutaraldehyde-fixation, tissue treatment with polysaccharide sulfates "sulfated polysaccharides" as for example chondroitin sulphate, use of a chitosan/heparin cross-linking treatment before or after fixation by glutaraldehyde, salts or polymers "mostly elastomeric polymers", using solutions rich in phosphate ester or quaternary ammonium salts or "sulphated higher aliphatic alcohol" after fixation with glutaraldehyde or association of some of these methods. Different cross-linkings have been proposed: (for example U.S. Pat. No. 7,579,381, 20050071926, U.S. Pat. Nos. 6,214, 054, 7,214,344, 20090164005). Example of other coupling agents or cross-linking: Sulfo-NHS (for example U.S. Pat. Nos. 7,479,164, 5,733,339), Triglycidylamine (TGA) (see U.S. patent 20030196274, U.S. Pat. No. 7,156,881), Bis-maleimide (see U.S. Pat. No. 6,596,471), Genipin (for example U.S. patent 20020091445, U.S. Pat. Nos. 6,998,418, 6,545,042), epoxide (for example U.S. Pat. Nos. 7,014,655, 6,106,555, 5,080,670), other coupling agents (for example U.S. Pat. Nos. 5,094,661, 5,002,566, 4,976,733, 5,679,112, 5,447,536, 5,368,608, 6,322,593, 6,302,909, 6,623,1614, 6,193,749, 6,177,514, 6,156,531, 6,132,986, 6,093,530, 5,919,472, 20060207031, 200500719326, 2003010746, U.S. Pat. No. 6,471,723).

Other associated treatments: de-cellularized tissues can be used (for example U.S. patent 20040052830, 20030228692, U.S. Pat. Nos. 5,632,778, 5,613,982. In addition to the cross-linking agents or cross-linking of other chemical or physical or biological agents as enzymatic can be associated as reducing agents, detergent type agents, agents aiming to de-cellularize the original tissue, agents aiming to remove lipids (for example U.S. Pat. No. 6,350,732, 20040253291), to improve glutaraldehyde-fixation by making it irreversible (for example U.S. Pat. No. 6,479,079).

The different methods of cross-linking, treatments or methods can be associated.

3) Manufacture of the Bioprosthetic Device from Animal Tissue with Animal ABH/Human ABH-ABO Phenotype Determined and Fixed/Cross-Linked:

In this invention, we propose manufacturing of an implantable device like a valvular bioprosthesis with tissue obtained previously. Tissue with determined ABH is then transported into a sterile room and processed, refined or configured and assembled or attached to any biological or non-biological component (for example stent, support, body rise, annulus, conduit, polyester mesh segment etc. . . . ) to form a bioprosthetic device. The bioprosthesis consists of three valves, one aortic valve of pig attached to a circular metal frame made of cobalt and chromium alloy with three body rise reproducing the commissures of the aortic annulus. This stent is flexible so as to partially offset the stress on the valve particularly in the commissures. The three valves are cut from the aortic butt, cleared at maximum of surrounding structures, and the rest of the muscle directly embedded into the wall of the stent. The collarette is made of silicon and is covered like any braided PTFE stent. In the other case, the bioprosthesis does not need to be reconstituted because the entire aortic pig butt will be used in one-piece (including the aortic sigmoid, the annulus and the aortic sinus).

Other bioprostheses can be made from tissue obtained previously. Non-exclusive examples of these devices are: bioprosthesis with stent: The valve of Carpentier-Edwards porcine (Edwards lifescience) marketed since 1975 initially fixed with glutaraldehyde, and then since 1984 fixation by glutaraldehyde and a treatment by Formaldehyde, Ethanol, Tween. The valves Carpentier-Edwards® stented porcine bioprosthesis, bioprosthesis made of ox pericardium (see Carpentier-Edwards® pericardial Bioprosthesis™), Hancock valve (Medtronic™) porcine bioprosthesis fixed with glutaraldehyde 0.625% (Hancock I™) or Glutaraldehyde and surfactant dodecyl sulfate (Hancock II™), Mosaïc™ valve (Medtronic™) porcine bioprosthesis glutaraldehyde with alphaoleic acid low pressure fixation, Biocor™ valves and Epic™ (Saint Jude™), Mitroflow™ valve (Carbomedix™), Pericarbon™ valve (Sorin) calf pericardium fixed with glutaraldehyde and post-treatment with homocysteic acid base, supra annumaire model Soprano™, stentless aortic porcine prosthesis (see Edwards®), Valve Free Style™ (Medtronic™) pig aortic root fixed with glutaraldehyde with alphaoleic type anticalcic agent, Valve Toronto™ (Saint Jude Medical™) pig aortic valve fixed in glutaraldehyde, valve Prima™ (Edwards™) pig aortic root fixed in low pressure glutaraldehyde, valve Pericarbon Freedoom™ (Sorin) valve formed by assembling of two layers of calf pericardium and glutaraldehyde fixation and homocysteic acid postfixation, Valve CryoLife—O'Brien™ formed of three porcine non-coronary sinus, ATS 3f™, bioprosthesis implementation by endovascular route (Core Valve™ (CoreValve, Inc, Paris, France) (WO03079929).

Main current cardiac bioprostheses: "Surgical Technology International" www.Surgicaltechnology.com STI XV Cardiovascular surgery "Advanced Technologies for cardiac valve replacement, transcatheter innovation and reconstructive surgery" W. R. Jamieson E, Hancock standard and Carpentier-Edwards standard, Carpentier-Edwards Supra-Annular (SAV) Aortic Porcine Bioprosthesis, The Carpentier-Edwards PERIMOUNT pericardial bioprosthesis (Edwards Lifesciences, Irvine, Calif., USA), Carpentier-Edwards Duraflex Low-Pressure Mitral Bioprosthesis, Carpentier-Edwards PERIMOUNT Magna Aortic & Mitral Bioprosthesis, Carpentier-Edwards PERIMOUNT Plus Mitral Pericardial Bioprosthesis, Carpentier-Edwards PERIMOUNT Theon Mitral Replacement System, Edwards Prima™ Plus Stentless Porcine Bioprosthesis, Carpentier-Edwards Biophysio Pericardial Aortic Bioprosthesis, The Hancock II porcine bioprosthesis (Medtronic, Inc., Minneapolis, Minn., USA), The Medtronic Mosaic™ porcine bioprosthesis (Medtronic, Inc., Minneapolis, Minn., USA), The Medtronic Mosaic Ultra™ (Medtronic, Inc., Minneapolis, Minn., USA), Medtronic Freestyle™ Stentless Porcine Bioprosthesis, The Medtronic-Venpro Contegra™ pulmonary valved conduit (Medtronic, Inc., Minneapolis, Minn., USA), the St. Jude Medical-Biocor porcine bioprosthesis (St. Jude Medical, Inc., Belo Horizonte, MG, Brazil), St. Jude Medical-Biocor Supra Porcine Bioprosthesis, The St. Jude Medical Epic porcine bioprosthesis (St. Jude Medical, Inc., St. Paul, Minn., USA, St. Jude Medical Epic Supra Porcine Bioprosthesis, The St. Jude Medical-Toronto SPV stentless porcine bioprosthesis (St. Jude Medical, Inc., St. Paul, Minn., USA), the St. Jude Medical-Toronto Stentless Root™ porcine bioprosthesis (St. Jude Medical, Inc., Minneapolis, Minn., USA), the St. Jude Medical-Biocor pericardial bioprosthesis (St. Jude Medical, Inc., Belo Horizonte, MG, Brazil), the St. Jude Medical-Biocor stentless porcine bioprosthesis (St. Jude Medical, Belo Horizonte, MG, Brazil), the St. Jude Medical Trifecta™ pericardial bioprosthesis (St. Jude Medical, Inc., St. Paul, Minn., USA), the Sorin Pericarbon™ MØRE pericardial bioprosthesis (Sorin Biomedica, Saluggia, Italy), the Sorin Pericarbon™ Freedom stentless pericardial bioprosthesis (Sorin Biomedica, Saluggia, Italy), the Sorin Pericarbon™ Freedom Solo stentless pericardial bioprosthesis (Sorin Biomedica, Saluggia, Italy), the Soprano supra-annular aortic pericardial bioprosthesis (Sorin Biomedica, Saluggia, Italy), the Mitroflow pericardial bioprosthesis (Sorin-Mitroflow, Richmond, British Columbia, Canada), the CryoValve Aortic valve with or without conduit (Cryolife International, Inc., Kennesaw, Ga., USA), the CryoValve Mitral valve (Cryolife International, Inc., Kennesaw, Ga., USA), the Cryolife-O'Brien stentless porcine bioprosthesis (Cryolife, Inc., Kennesaw, Ga., USA), the Shelhigh Skeletonized Super-Stentless™ (Shelhigh, Inc., Union, N.J., USA), the BioMitral™ valve (Model NR-900), the current generation Shelhigh porcine pulmonic valve conduit (Shelhigh, Inc., Union, N.J., USA), the Koehler Aspire porcine bioprosthesis (Koehler, Bellshill, Scotland), the Koehler Elan stentless aortic porcine bioprosthesis (Koehler, Bellshill, Scotland), the Koehler Root Elan stentless aortic porcine bioprosthesis (Koehler, Bellshill, Scotland), the 3F Therapeutics™ bioprosthesis (3F Therapeutics Inc., Lake Forest, Calif., USA), the Labcor stented porcine bioprosthesis (Labcor, Inc., Belo Horizonte, MG, Brazil), the Labcor stented pericardial bioprosthesis (Labcor, Inc., Belo Horizonte, MG, Brazil), the Labcor stentless porcine bioprosthesis (Labcor, Inc., Belo Horizonte, MG, Brazil), the Glycar Quattro™ mitral bioprosthesis (Glycar, Inc., Johannesburg, South Africa).

Main patents corresponding to these inventions non-exclusively: different methods for production of aortic bioprosthesis (for example U.S. Pat. Nos. 7,316,712, 6,391,538, 20020173843, 5,824,061, 20090030511, U.S. Pat. Nos. 6,254,636, 6,086,612, 6,719,789, 6,074,417, 7,011,681, 6,530,952, 5,824,067, 20040024452, U.S. Pat. Nos. 5,769, 780, 4,692,164, 4,626,255, 20080154358, U.S. Pat. Nos. 5,824,060, 7,166,124, 7,163,556, 6,540,781, 5,728,152, 5,571,174, 5,549,665, 5,352,240), mitral, pulmonary U.S. Pat. No. 7,320,705, tricuspid, with or without stent (for example U.S. Pat. Nos. 5,156,621, 5,080,670, 4,626,255, 4,561,129, 4,388,735, 4,378,224), with absorbable stents (for example U.S. Pat. No. 5,489,297 with or without suture (for example 20030196274, 20030181974, U.S. Pat. Nos. 7,322, 932, 6,027,530, associated or not associated with stents (for example 20090118826) for endovascular implantations (for example 20030125805, 20030125793, U.S. Pat. Nos. 7,125, 418, 7,318,998, 7,041,132, 7,033,390, 6,719,785, 6,682,558, 6,087,552, 5,755,782, 554,521) or by mini-invasive surgery have been reported. Also, the ways to set the layers to form valves. Possibility of manufacturing valves. Support systems (for example US Patent 20010002445). Possibility of using physical stimulation during the manufacture of bioprostheses (for example U.S. Pat. No. 7,348,175). Valve repair system (for example U.S. patent 20040143323, U.S. Pat. No. 7,455, 689) or to manufacture the bioprosthesis in situ (for example U.S. Pat. No. 5,326,370) (The Edwards Lifesciences percutaneous aortic heart valve (Edwards Lifesciences, Irvine, Calif., USA) The CoreValve percutaneous pericardial aortic valve (CoreValve, Irvine, Calif., USA) Medtronic Melody transcatheter pulmonary valve (Medtronic Inc., Minneapolis, Minn., USA) The ENABLE™ Aortic Bioprosthesis (3F Therapeutics, Lake Forest, Calif., USA) The ENTRATA™ transventricular aortic bioprosthesis (3F Therapeutics, Lake Forest, Calif., USA) The Edwards Ascendra™ valve replacement system (Edwards Lifesciences, Irvine, Calif., USA) The Sadra Percutaneous pericardial aortic valve (Sadra Medical, Campbell, Calif., USA) i The AorTx (AorTx, Palo Alto, Calif., USA) concept The Corazón PAVR system (Corazón Technologies, Menlo Park, Calif., USA) The Corazón Surgical Aortic Valve Repair (SAVR) System (Corazón Technologies, Menlo Park, Calif., USA) Percutaneous bioprostheses for tricuspid regurgitation (3F Therapeutics, Lake Forest, Calif., USA)).

Example of other bioprosthetic devices: (partial list): possibility of making patch matrices (for example U.S. Patent 20010051824, 20040157206, U.S. Pat. Nos. 6,652,583, 6,174,333, 5,855,620, 6,517,576), Cook Biotech Inc, West Lafayette, Ind., USA, SMJ™ Pericardial Patch with EnCap™ Technology St Jude Medical™), vascular conduits (for example U.S. Pat. No. 5,545,215, 20040158320, 20010020191, U.S. Pat. Nos. 6,358,275, 6,206,917, 6,110, 212, 6,087,552), valves conduits (for example U.S. Pat. No. 5,376,112) or to treat biological tissues (for example US patent 20060207031).

Bioprosthesis can be a scaffold, as for example a scaffold described in PCT/FR2008000785. This scaffold can be cellularized; It can be used for cell therapy, regeneration, replacement, tissue reconstruction including skin. The three-dimensional scaffold is totally or partially non-biodegradable. The three-dimensional scaffold is formed in a liquid phase which, once delivered, after or without activation can transform into solid phase (for example solution, paste, gel, colloidial suspension, plasma). The three-dimensional scaffold can be made of a hydrogel composed of hydrophobic and hydrophilic amino acids capable to assemble itself spontaneously into macroscopic structures. The three-dimensional scaffold may be a gel or a surfactant. The three-dimensional scaffold where the scaffold is a surfactant or an "intelligent agent", i.e. a biological matter made of spontaneously assembled structures on a large scale based on local interactions at the molecular level. In the three-dimensional scaffold, 3D construction can be obtained by superimposition of cultures obtained on different 2D scaffolds. The adhesion of cells to this 2D support can be modulated. These 2D supports can contain collagen/fibrin/fibrinogen modified by fixation of adhesion molecules. Several different type 3D scaffolds can also be superimposed sequentially or not. The three-dimensional scaffold can form a matrix of cells where the construction of artificial tissue contains biomaterials of chosen forms facilitating the structural grouping: micro or nano structures (for example micro or nano tubes, nano-particles, micros or nanopores). Microparticles or nanoparticles are made of silicon, poly—(lactic acid) mixture of acid-Co polymer—lactic glycolic acid, cyclodextrin, liposome conjugated or not with nanoparticles quantum dot, magnetite, filaments, structural analogues to form the external interface, peptide analogue structures β-/or-α structures which form filaments or tubes, sponge, powder, conduit, sphere, microsphere, film, micro or nanofibrils, lipid membrane, fiber, mesh, matrix, patch, tissue layer, interlining or combination.

Other bioprosthetic devices such as (for example U.S. Pat. Nos. 5,067,962, 6,936,070, 6,790,213, 4,585,458, 7,404,819), The Shelhigh BioRing (Shelhigh, Inc., Milburn, N.J., USA) Prima™, Restore™, Oasis™, Surgisis™, Cuff-Patch™, GraftJacket™, Alloderm™ TissueMend™, Orth-Adapt™. The device can also be collagen injectable or not (for example U.S. Pat. Nos. 6,548,077, 6,127,143, 5,814,328, 5,374,539), for example compressed tissue (for example U.S. Pat. No. 7,141,064). It can be used for regeneration, replacement, tissue reconstruction as for example in reconstructive surgery with bioprostheses manufactured from pig cutaneous tissues.

The various devices described above can be associated.

Principles Governing the Phenotypic Compatibility Rules in ABO/ABH System

Thus, this is for a given patient of "ABO phenotype" to implant a tissue or tissue extract likely to induce least of possible reactivity by ensuring that the ABH phenotype of bioprosthetic device is "compatible" with the ABO system of the patient.

The phenotype is the one expressed in the bioprosthetic device at the time of its implantation and which can be different from the ABH phenotype of the animal or animals in which the tissues were prepared. Depending or not depending on the presence of the antigen A, B, the individuals have or do not have an immunological reactivity in their blood vis-a-vis the missing antigen. This reactivity is expressed by the presence of these individuals of antibodies vis-a-vis the missing antigen in the blood. Apart from the individuals of "Bombay group" who do not have H antigen and thus no group A and B and thus have anti H, anti A and anti B antibodies, all being humans express the H specificity. Therefore, they do not have anti H antibodies. Patients of group thus have anti B reactivity but accept H or A tissues. Patients of group B have anti-A reactivity but accept B and H tissues. Patients of group O have anti A and anti B reactivity and accept type H tissue. Patients of group AB do not have anti A, anti B or anti H reactivity and thus accept A, B or H tissues. Patients of "Bombay group" have anti A, anti B and anti H reactivity. The reactivity is vis-à-vis the Human A, B, H antigen. If there exist an identity for the antigen A and to some extent with the antigen H in humans and in some animals such as pig for example, this is not true for antigen B which is different. Individuals of human B group will therefore develop an immunological reaction vis-à-vis the animal B group tissue. For other blood groups expressed in pigs particularly group I which is frequently found in pigs not expressing the antigenicity A, individuals will develop a reactivity vis-a-vis that antigen.

The different antigenicities have been defined previously.

This invention is further illustrated, without being limited, in the following examples.

EXAMPLES

Example 1

Obtaining an Animal Tissue with a Determined Animal ABH/Human ABO-ABH Phenotype

In example 1, we have used the property of some pigs to express the A antigenicity in their tissue for obtaining tissues with "human A phenotype" but other approaches to obtain tissues with a given specificity have been described previously in the patent.

In example 1, we have used PCR on valvule extract DNA of pig for detecting human transferase A activity which encodes for the A specificity by using the DNA extraction kit from Invitrogen™ and the DNA has been amplified by using 3 pairs of "primers" known for amplifying the human A1 genes (56). But other primers may be used like FY-520 (5'-CCG-GAATTCAACACTTCATGGTGGGACAC-3'—SEQ ID N° 1) and FY-521 (5'-CCGGAATTCTA GCTCTCATCATGC-CACAC-3'—SEQ ID N° 2). Other approaches like histological approaches may be used for phenotyping the pigs.

A. Method for Obtaining the ABH Phenotype of an Animal Tissue:

The method for identification of ABH groups in animals is relatively common and many of the techniques applied to ABO phenotype in humans are applicable in animals. The techniques used in pigs may be extended to other species, particularly ox. Indeed, the ABO/ABH system is a system which is highly preserved during the evolution.

B. Detection of Pig's Blood Group:

To determine the pig's blood group, take 0.5 ml of pig blood and 0.5 ml of PBS in heparin tube. Add 25 micro liter of diluted blood and put it in one Eppendorf tube for centrifugation. 25 micro-liter of mouse anti-human A antibody is incubated, incubated at an ambient temperature for 5 minutes, and then centrifuged at 900 g for 3 minutes. After centrifugation, hemagglutination is observed under a conventional microscope. The incubation with human anti B antibodies acts as negative control (51).

There is an ABH tissue system in parallel in pigs and in several animals with some correlation between the ABH blood and tissue system (43).

Some tissues are more prompt than others to express ABH antigens. The exocrine tissues, epitheliums of digestive tube, urinary system especially kidneys, genital system including testicle, salivary glands.

C. Detection of AH Group of Pig on Fixed Tissues:

Biopsy of kidneys has been frozen in O.C.T. medium of cryo-freezing (Miles, Inc., Elkhart, Ind., USA) in nitrogen liquid. The samples have been cut and then preserved at −80° C. The sections have been secondarily fixed with cold acetone for 10 minutes, dries in ambient air and then rehydrated in PBS for 7 minutes. For limiting the basic noises, the slides have been incubated for a period of 15 minutes with different agents, 3% hydrogen peroxide (Sigma) and avidin (Dako-cytoformation) protein blocking agents (Thermo, Electron, Pittsburgh Pa., USA). Between each block, rinse for 10 minutes. The slides have been then incubated at ambient temperature for 30 minutes with a primary anti A or anti H antibody (DakoCytoformation). After washing, the sections have been secondarily incubated with a secondary antibody with a "biotinylated" sheep anti-mouse antibody for 30 minutes (DakoCytoformation). The coloured reaction has been achieved by using 3-amino-9-ethylcarbazole which will react with the peroxidase for giving a red colour and the slides also have been marked with H~SE (Eosin hematoxylin) (51). Another solution using a fixation with paraformaldehyde then a treatment with microwave and then using non biotinylated detection kit (Vision detection kit HRP/DAB (Dako, H5007)) (58).

The detection of H antigen may be done by using a specific *Ulex Europaeusl* lectin (UEAI) (Vector Laboratories, Burlingame, Calif., USA) or anti-H anti-H1 or anti-H2 antibodies (see Oriol Transplant international 1994). The pig I antigen may also be identified by using lectins like Galactose-specific lectin rictin lectin ($RCA_{120}$) (52), *Arachis Hypogaea*, *Helix pomatia* (HPA San Mateo Calif. USA) and antibodies for group A. Globally, in large white pigs breed (analysis on 37 pigs), 51% of pigs are of group A (Marking) antibodies. 38% are not recognized by anti A but however expresses the H chain, especially of type 2 recognized by UEAI lectin. Finally, 11% of pigs are A− and H− but are recognized by another lectin (see *Arachis Hypogaea* (PNA) and anti-I+ antibodies), are generally $le^{y-}/le^{x+}$.

However, it even exist in the pigs of type A, a certain number which are also I+. The type A pigs are generally H− because they do not react with UEA 15/19. However, there is 3/19 of these pigs which express the human H and A antigen. They are A+/H+/I−. There is also phenotype A 6/19 ~30% among these pigs which are not purely group A and which also express group I specific to pigs. These pigs are A+/H−/I+ (49).

Generally, the pigs which are H+ also express Lewis specificity and are generally $le^{x-}/le^{y+}$. For the A−H+ 3/14 group are also I+ (49). In another Busch J. analysis on the biopsies of pig's kidney (Large White/Landrace/Duroc) cross-breed pigs show that A+ 8/11 with 2/8 (25%) A+H+. Others 3/11 are A−H+ (51).

To determine the type of H1 or H2 core from the H chain, the resistance of pigs to different toxins "heat labile toxin from *E. Coli*>>(LTs) or Cholera (CT) for example may be used (we can also use specific anti-H1 or anti-H2 antibodies or on the tissues of these animals or on proteins secreted by these animals). The capacity of proteins purified from the secretions present on the surface of pig's intestine to fix these toxins would be directly linked to H1 or H2 phenotype of H core of the considered pig. In the absence of fixation, this is pig I. Fixation of LTs, only core H2. Fixation of LTs and CT, this is core H1. This type of approach can be a rapid way to identify the pigs for their H phenotype because of a more or less larger resistance to the infection (52, 59, 60) or by some behaviour like for example, the size of the litter (61). The *E. Coli* has a receptor who specifically recognizes the H1 A cores. This property could also be used for identifying the core H1 pigs (62).

We can also be interested in the Lewis specificity of these animals, mostly on biopsy of testicles in animals aged more than 3 weeks (possibility of using especially the anti $le^x$ or anti $le^y$ antibodies). The Lewis specificity is encoded by FUT2 gene which also encodes for H2 type core of the H chain. The gustatory glands also allow detecting the majority of panel of ABO antigens (63).

The tissues are fixed with 10% formalin and included in paraffin for sections. After deparaffinization, the sections were incubated for 30 minutes in a humid chamber with fluorescein and rhodamine-conjugated lectins 20 mg/ml and then shown in medium for fluorescence (Vector Laboratories, Burlingame, Calif., USA) and examined under fluorescence microscope (43, 49).

The detection can be done in biopsies of several tissues, especially exocrine tissues, genitourinary system (51), digestive tubes (49), digestive system. For review Nishi K. et al. 2005 ABO Blood Typing (64).

D. Detection of ABH Phenotype on the Animal Secretion Products

It is also possible to do analysis of H substances on the secretions themselves like for example milk (65), submaxillary secretions, bronchial mucus. The ABO groups are often associated with mucins. Possibility of identifying different forms by HPLC (36) or western Blott with use of specific anti H1 antibodies (Clone 17-206 Signet Dedham Mass., USA) or anti H2 clone 92 FR-A2 Dako Carpinteria, Calif., USA) or $Le^b$ (Clone T218 Signet Dedham Mass., USA), $Le^a$ (clone KM231 Calbiochem-Novabiochem San Diego Calif.), $Le^x$ (Clone P12 Calbiochem-Novabiochem San Diego Calif.)

(Clonex (65). If the majority of pig secrete type H1 cores H in their milk, the secretion of type H2 core H is more restricted (65).

E. Detection of AH Group of Pig on the Epithelial Cells of Mucosa:

Another easier technique is to do a phenotyping on the epithelial cells of buccal mucosa by rubbing the buccal mucosa with cotton and applying this cotton on a glass slide. The specimens are left to dry at an ambient temperature. The slides are fixed with cold acetone (Sigma, St Louis, Mo., USA) for 10 minutes and then rehydrated in PBS. Human anti-mouse antibody A 1/50 Dilution, H1/50 dilution IgM monoclonal antibody (DakoCytoformation, Carpinteria, Calif., USA) is applied 100 microliter in a humidifying chamber for 60 min. in dark with sheep anti-mouse conjugated FITC antibody 1/100 (Vector, Burlingame, Calif., USA) is observed with a florescence microscope (51).

F. Detection of ABH Systems on Appendages:

The A antigen has been shown as expressed inside the appendages like hair (64).

G. Genotyping of Animals for their ABH System:

Because of the complexity of ABO groups, the molecular biology techniques (31-34) risk, in some years, to replace the current technique by serology. These techniques may be used in the animal (66).

It is also possible to perform phenotyping of pig by genotyping (56, 57, 63, 67-69). The entire development of these sugars is under the control of different enzymes encoded by genes. In a very interesting manner, the genes encoding for these different activities have been conserved highly during evolution so that in many cases, human primer sequences that we used to sequence this and that gene can be used in the animal. This is particularly the case for endo-galactosidase gene A (A1 or A2) which encodes for the human A antigen (67). For the H specificity, it is possible to be interested particularly in FUT 1 and 2 genes (42, 60, 70-72). The "genotyping" for ABH groups in animals has been carried out on secretions like saliva (67), blood, on DNA tissue extract such as submaxillary tissue in the pig (57). Genotyping can be searched on the ABO group but also the secretor non secretor status (73).

The different techniques previously described will allow identifying the pigs useful because of their ABH specificity. Especially A+ (A+H+I->A+H-I->A+H-I+) pigs, and H+ (A-H+I->A-H+I+) pigs and other pigs particularly I (A-H-I+) pigs. The results can be possibly confirmed on histological section of tissue. This approach may be accompanied by a phenotype of core H eventually by genotype on the submaxillary glands for example.

The bioprostheses will be then proposed for example according to the type H1 or H2 phenotype of core H of the patient. As we have seen previously, there is a direct relationship between the type of core H, H1 or H2 and the secretor phenotype or not of the patient and its characteristics for $Le^a$ or $Le^b$ Lewis group.

Example 2

Fixation/Cross-Linking of Tissue with Animal ABH/Human ABO-ABH Phenotype Determined Porcine valvular tissues previously removed in the pig of type A+ or A− in example 1 have been immersed in glutaraldehyde solution 0.625% in PBS pH 7.4 with a controlled temperature 37° C. for a duration of 2 weeks and then subject to a treatment by denaturant/surfactant and cross-linking agent (see formaldehyde 4%, Ethanol 2.2% and Tween 80 1.2% respectively) for 3 days.

Different possibilities of tissue fixation have been described previously and can be used instead of the fixation that we have used like for example, non-exclusively, different types of treatments for fixing the tissues as described previously. Through example of fixation alternatives for glutaraldehyde (U.S. Pat. Nos. 7,579,381, 7,214,344, 6,878,168, 6,561,970, 6,547,827, 6,214,054, 6,008,292, 5,935,168, 5,931,969, 5,782,931, 5,215,521, 4,885,005, 4,838,888, 4,648,881, 4,647,283, 20070255423, 20060217805, 20040253291, 20070255423, 20050071926, U.S. Pat. No. 7,214,344, 20090164005).

Example 3

The Knowledge of ABH Phenotype of Cross-Linked Tissue Allows Obtaining Bioprosthetic Tissues which Calcify Less in the Receiver Depending on its ABO/ABH Group The rats like pigs express B or AB antigenicity. The porcine tissues previously fixed for A+ or A− phenotype have been implanted subcutaneously in Wistar rats of ABH phenotype A+ (see AB) or A− (see B) in a sterile manner.

The phenotype of rats which have been implanted has been determined by making a histological marking on biopsy of submandibular glands. The submandibular tissues have been fixed with 10% formaldehyde put in paraffin and 5 micrometer sections have been made. Anti A antibodies (ortho diagnostic, Ranitan N.J.) have been used as described previously. (see *J. Of Forenscic Medicine and toxicology* 2001, 20, n° 2 Nishimura A).

The calcification of implants has been measured by spectroscopic absorption after 30 days of subcutaneous implantation in the rat. n=10 per group Calcifications porcine A+ implants in the rats A− 135+/−22 µg Ca/mg dehydrated tissue. Calcium porcine A+ implants in the rats A+ 30+/−7 µg Ca/mg dehydrated tissue.

This example shows how the knowledge of ABH phenotype of the original tissue allows obtaining the devices which will have the less tendency to calcify if we know the ABO/ABH group of the receiver and if the allocation is done according to the criteria that we have defined.

Example 4

Results of Porcine Bioprosthetic Devices According to ABO Phenotype of Implanted Patients 4.1 Involvement of ABO Phenotype of Patients in the Longevity of Bioprosthesis:

Currently for a given individual, there are only very few parameters for predicting the longevity of a bioprosthesis. For the allocation of a bioprosthesis, we consider the implantation site for the age, configuration of the implantation site (gradient, space requirement) but the parameters specific to the subject such as its immunological reactivity are not considered.

In the following study, we provide the proof that the knowledge of ABO group allows determining the reactivity of the subject vis-à-vis the ABH sugar residues carried by the bioprosthetic device and that by considering this reactivity and by adapting the devices, it is possible to obtain devices with a greater longevity with lesser early failure and lesser tendency to the calcification.

"Carpentier-Edwards standard" type porcine bioprostheses (treatment by glutaraldehyde or glutaraldehyde treatment plus "sterilising treatment (see formaldehyde/Ethanol/Tween") manufactured from pig of type A+ or A– have been implanted in patients of group A, O, B, AB.

During the implantation and production of the bioprosthesis, the phenotype of the pig was not searched because we did not know how we show it in this invention that the ABH group of the pig could have an influence or that the ABO group of the patient could have an influence on longevity of the bioprosthesis.

Given the frequency of phenotype A in the pig around 30%, a patient of group A had a chance on 3 of receiving a bioprosthesis manufactured in an animal corresponding to it phenotypically. This went to 1/6 with the bioprosthesis manufactured from two pigs as this was the case for some marketed bioprosthesis.

Thus, we have investigated all the bioprostheses explanted due to degeneration over a time span of 10 years. This represents a number of around 920 patients. In these patients, the different factors reported to influence the longevity of bioprostheses (Age at implantation, sex, diameter of the bioprosthesis, type of bioprothesis, implantation site (Aortic/mitral/tricuspid), number of bioprothesis implanted as well as the ABO group of patients have been searched. There were 52% men, implantation site 62% aortic, 36% mitral, 2% tricuspid position. Number of bioprostheses implanted n=1 82%, n=2 17%, n=3 1%. Longevity of the bioprosthesis <6 years (10.4%); [6-9] (27.3%); [9-12] (35.5%); [12-14] (13.9%); >14 (12.8%). The distribution of ABO groups in the patients with degenerative bioprostheses 36.3% A, 42.4% group O, 15.2% group B, 6.1% group AB. In the Caucasian population from where these patients came, the distribution of ABO groups is group A>40%, group O>40%, group B<10%, group AB ~3% respectively. In our population of re-operated patients, there were proportionally fewer patients of group A, the % of patients of group O is normal and however groups B and AB are found increased which is consistent with one more impact of re-operations in the patients of group O, B or AB compared to the patients of group A.

We then performed a multi-varied analysis on all the risk factors conventionally reported as having an impact on longevity of the bioprosthesis so far including in addition the ABO group of patients. Use of SEM software.

We found two independent variables to explain the longevity of bioprostheses (see Table 1). The blood group of the patient, the implantation site and the number of bioprostheses implanted. In a very interesting manner, the most important factor in the model is the ABO group of patients.

TABLE 1

Multi-varied analysis of longevity factor of porcine bioprosthesis: Group A involvement compared to other groups

| Longevity | Coeff. | Std Err. | t | P(t) | Interval. 95% |
|---|---|---|---|---|---|
| Group A | 0.79 | 0.33 | 2.33 | 0.02 | 1.45 |
| Implant. Age | −0.01 | 0.01 | −0.94 | 0.34 | 0.01 |
| Sex | 0.25 | 0.32 | 0.78 | 0.43 | 0.88 |
| Mitral Site | −0.76 | 0.33 | −2.30 | 0.02 | −0.11 |
| Bio. number | −0.44 | 0.35 | −1.25 | 0.21 | 0.25 |

Regardless of all other factors, the patients of group A have longevity of the bioprosthesis 2.33 years greater than the patients of other groups. This difference is already major because it comes out first in the multi-varied analysis with the most significant weight. It is of the same significance as the implantation site of the bioprosthesis (mitral/aortic implantation site) which is a data undeniable and recognized by all clinician in its choice for the implantation of a bioprosthesis.

The difference that we report considerably underestimates the expected benefit. Indeed, according to the breed of original pigs, the impact of group A varies from 20-40%. Moreover, in group A, there are different phenotypes A+−H+−I− A+−H+−I−, but also A+−H−I+ ~30%. Hence, we can estimate that the difference observed is due to the patients of group A who have received pig tissues or only between 14% and 30%. The actual difference is probably 3× greater compared to the numbers that we report in terms of gain in years. This probability is still 2 times lesser for the patients of group A who will receive a bioprosthesis prepared from different pigs.

The patients of group O (table 2) do not have specially a prolonged longevity of their bioprosthesis compared to other groups. It is the same for groups B (Table 3) and AB (Table 4). Interestingly, even though group B shares some structural similarities with the major xenorecativity antigen: "alphaGal", the patients of group B do not have a specially marked longevity of their bioprosthesis.

TABLE 2

Multi-varied analysis of longevity factor of porcine bioprosthesis: Group O involvement compared to other groups.

| Longevity | Coeff. | Std Err. | t | P(t) | Interval. 95% |
|---|---|---|---|---|---|
| Group 0 | 0.27 | 0.31 | 0.86 | 0.38 | 0.88 |
| Implant. age | −0.009 | 0.01 | −0.84 | 0.40 | 0.01 |
| Sex | 0.17 | 0.32 | 0.54 | 0.59 | 0.80 |
| Mitral Site | −0.69 | 0.33 | −2.1 | 0.038 | −0.04 |
| Bio. number | −0.60 | 0.35 | −1.7 | 0.086 | 0.09 |

TABLE 3

Multi-varied analysis of longevity factor of porcine bioprosthesis: Group B involvement compared to other groups.

| Longevity | Coeff. | Std Err. | t | P(t) | Interval. 95% |
|---|---|---|---|---|---|
| Group B | 0.45 | 0.44 | 1.04 | 0.30 | 1.33 |
| Implant. age | −0.009 | 0.01 | −0.82 | 0.41 | 0.01 |
| Sex | 0.18 | 0.32 | 0.57 | 0.57 | 0.82 |
| Mitral Site | −0.70 | 0.33 | −2.14 | 0.033 | −0.06 |
| Bio. number | −0.61 | 0.35 | 0.35 | 0.082 | 0.08 |

TABLE 4

Multi-varied analysis of longevity factor of porcine bioprosthesis: Group AB involvement compared to other groups.

| Longevity | Coeff. | Std Err. | t | P(t) | Interval. 95% |
|---|---|---|---|---|---|
| Group AB | −0.38 | 0.68 | −0.55 | 0.58 | 0.97 |
| Implant. age | −0.009 | 0.01 | −0.84 | 0.40 | 0.01 |
| Sex | 0.18 | 0.32 | 0.58 | 0.56 | 0.81 |
| Mitral Site | −0.72 | 0.33 | −2.17 | 0.03 | −0.06 |
| Bio. number | −0.56 | 0.35 | −1.6 | 0.11 | 0.13 |

In this invention, we will show the involvement of ABO groups in longevity of the bioprostheses. We show how the consideration of ABO groups of patients as reactivity markers vis-à-vis less xenogeneic tissue allows obtaining medical/surgical devices like bioprostheses with considerably improved longevity for a given patient. The gain in longevity largely exceeds all results obtained until then with different types of bioprostheses which have been developed and marketed.

4.2 In this Invention, we Will Show how the Knowledge of ABO of Patients is a Key Factor for Determining the Bioprostheses which Will have Longevity Considered as Exceptional or Unexplained Early Failures.

In this invention, we will show how the consideration of ABO group of patients allows obtaining in a given patient, by admitting that he receives the device with a suitable ABH phenotype, devices with extended life and limit the early failures due to an early impairment of bioprostheses before 7 years. This allows making devices more secured in terms of results, at the same time better in the long term, with least early failures.

We have separately analysed the bioprostheses group with exceptional longevity beyond 16 years by including all the known factors to explain the longevity of bioprostheses and the ABO group of patients.

Once again, as table 5 shows, the ABO group of the patient is, in multi-varied analysis, the main predictive factor of an exceptional longevity of a bioprosthesis for more than 16 years. What is also very important is that group A still appears as the most important predictive factor for longevity of bioprostheses in the long term before even the implantation site. Once again, the type of implanted bioprothesis does not appear as a significant predictive variable of an extended longevity of the bioprosthesis in this analysis.

TABLE 5

| Longevity > 16 years | Coeff. | Std Err. | t | P(t) | Interval. 95% |
|---|---|---|---|---|---|
| Group A | 2.3 | 1.0 | 1.97 | 0.048 | 5.6 |
| Implant. age | 0.99 | 0.01 | −0.66 | 0.50 | 1.0 |
| Sex | 2.28 | 1.01 | 1.85 | 0.064 | 5.4 |
| Mitral Site | 0.23 | 0.10 | −3.15 | 0.002 | 0.57 |
| Bio. number | 1.28 | 0.57 | 0.56 | 0.57 | 3.0 |

The consideration of ABO group also allows limiting the impact of early impairment of bioprostheses before 7 years. In the same way, the patients of group A have a lower risk of early degeneration of their bioprosthesis (before 7 years) than the patients of other groups.

4.3 In this Invention, we Will Show how the Reactivity of Patients Vis á Vis Sugar Residues Carried by the Bioprosthesis can Explain the Propensity of Bioprostheses to Calcify.

At the time of explanation, the calcified or non calcified status of the bioprosthesis has been colligated. It is necessary to know that there are other types of degeneration for the bioprostheses particularly with lacerations or formation of a pannus.

Different factors have been reported for explaining the tendency to calcification, especially age of the patient at implantation with a specifically fast calcification in the young subject, the period of implantation of the bioprosthesis. We will still show the importance of ABO group with lesser tendency to calcification for the patients of group A (coeff. <1. See Table 6)

TABLE 6

| Calcification O/N | Coeff. | Std Err. | t | P(t) | Interval. 95% |
|---|---|---|---|---|---|
| Implantation period | 0.96 | 0.02 | −1.16 | 0.24 | 1.02 |
| Group A | 0.72 | 0.15 | −1.55 | 0.12 | 1.08 |
| Implantation age | 0.96 | 0.006 | −4.87 | 0.0002 | 0.98 |

The results of multi-varied analyses comparing other groups O with respect to other groups, B and AB are reported in table 7. If the effect of group O on calcification is indifferent, the patients of group B and AB have a stronger tendency to calcify their bioprosthesis (see coeff.>1 1.3 and 1.12 (greater than 1) respectively).

TABLE 7

| Calcification O/N | Coeff. | Std Err. | t | P(t) | Interval. 95% |
|---|---|---|---|---|---|
| Group O | 1.0 | 0.04 | 0.18 | 0.96 | 1.4 |
| Group B | 1.3 | 0.36 | 1.10 | 0.79 | 2.2 |
| Group AB | 1.12 | 0.46 | 0.28 | 0.78 | 2.5 |

Example 5

ABH Phenotype of Bioprosthetic Tissue Must be Adapted to the ABO/ABH Phenotype of the Patient In addition to the implantation example in the animal (example 3), where we have shown that calcification of the bioprosthetic tissue in animals depends on its ABH phenotype and that of the implanted bioprosthesis, we have researched if this is also verified in humans. We have checked if exceptional results were not in fact linked to an adequacy by the coincidence between the ABH phenotype of the bioprosthesis and ABO phenotype of the patient.

We have researched on porcine bioprostheses with exceptional longevity (greater than 16 years) the ABH phenotype of pig from which the bioprostheses have been manufactured. Thus, we have extracted the DNA of explanted bioprostheses by using the Invitrogen Kit for extracting the DNA. We have then researched the expression of transferase A activity. The DNA has been amplified by using 3 pairs of "primers" described for amplifying the human A1 genes (56). If the gene encoding for porcine and human transferase A enzyme is identical, fragments of restrictions are different and it is hence possible in performing digestion of PCR products by EcoRI with or without BamHI (56) and migration on agarose gel to authenticate the source of transferase A activity. Thus, for a type A patient, it is possible to detect transferase A activity of porcine origin. Other markers expressed in pig and human but of different size like P53 gene have been used as control.

The analysis of different explanted bioprostheses with exceptional longevity has shown that the patients of group A who have a bioprosthesis with exceptional longevity have all received a bioprosthesis from type A pig. For some patients of groups B and O who have had a bioprosthesis with exceptional longevity, none had received type A bioprosthesis.

Thus, this analysis shows that it is essential to have an adequacy between the ABH phenotype of the animal tissue and the ABO phenotype of the patient.

Thus, this invention proposes bioprostheses suitable for ABO phenotype of the patients.

The invention claimed is:
1. A method for obtaining a bioprosthesis for implantation in a human patient, the bioprosthesis comprising chemically fixed substances from non-human animal tissue, the method comprising:
 a) providing one or more said bioprostheses, wherein a phenotype in the ABO/ABH system is known, and
 b) conditionally selecting a bioprosthesis for implantation depending on a relation between the ABO/ABH phenotype of the non-human animal tissue in the bioprosthesis and the ABO/ABH phenotype of the human patient, wherein the conditionally selecting comprises:
(i) if the ABO/ABH phenotype of the human patient is A, then selecting a bioprosthesis having a ABO/ABH phenotype of A or H;
(ii) if the ABO/ABH phenotype of the human patient is O, then selecting a bioprosthesis having a ABO/ABH phenotype of H;
(iii) if the ABO/ABH phenotype of the human patient is B, then selecting a prosthesis having a ABO/ABH phenotype of B or H,
(iv) if the ABO/ABH phenotype of the human patient is AB, then selecting a prosthesis having a ABO/ABH phenotype of A, B or H.

2. The method according to claim 1, wherein the substances from the non-human animal tissue are from a mammal.

3. The method according to claim 1, the bioprosthesis is a heart valve type bioprosthesis, an arterial bioprosthesis, a vascular bioprosthesis, a patch or tissue bioprosthesis, a pulmonary bioprosthesis, or a replacement tissue or regeneration tissues bioprosthesis.

4. The method according to claim 1, wherein the bioprosthesis is a heart valve selected from the mitral, aortic, tricuspid, and pulmonary valves.

5. The method according to claim 1, further comprising knowing or determining the phenotype in the Lewis system of the one or more bioprostheses and the human patient; and
wherein the conditionally selecting further comprises selecting a bioprosthesis having Lewis compatibility with the human patient.

6. The method according to claim 1, wherein the chemically fixed substances from non-human animal tissue are chemically fixed with a crosslinking agent.

7. The method according to claim 6, wherein the crosslinking agent comprises glutaraldehyde.

8. The method according to claim 2, wherein the mammal is pig, cow, sheep, kangaroo, seal, camel, or horse.

* * * * *